United States Patent [19]
Laus et al.

[11] Patent Number: 6,080,409
[45] Date of Patent: *Jun. 27, 2000

[54] IMMUNOSTIMULATORY METHOD

[75] Inventors: Reiner Laus; Curtis Landon Ruegg, both of San Carlos; Hongyu Wu, Palo Alto, all of Calif.

[73] Assignee: Dendreon Corporation, Mountain View, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/579,823

[22] Filed: Dec. 28, 1995

[51] Int. Cl.$^7$ .................. A61K 39/00; A61K 39/385; A61K 38/00; A01N 37/18
[52] U.S. Cl. ................. 424/192.1; 424/193.1; 424/194.1; 424/195.11; 424/198.1; 514/2
[58] Field of Search ............... 536/23.5; 435/320.1; 424/192.1, 193.1, 194.1, 195.11, 198.1; 514/2

[56] References Cited

U.S. PATENT DOCUMENTS

| | | |
|---|---|---|
| 4,861,589 | 8/1989 | Ju . |
| 5,019,384 | 5/1991 | Gefter et al. . |
| 5,078,996 | 1/1992 | Conlon, III et al. . |
| 5,194,254 | 3/1993 | Barber et al. . |
| 5,334,379 | 8/1994 | Pillai et al. . |
| 5,616,477 | 4/1997 | Price . |
| 5,677,171 | 10/1997 | Hudziak et al. . |
| 5,851,756 | 12/1998 | Steinman et al. . |

FOREIGN PATENT DOCUMENTS

| | | |
|---|---|---|
| 309 898 | 4/1989 | European Pat. Off. . |
| 0 406 857 A1 | 1/1991 | European Pat. Off. . |
| WO 91/13632 | 9/1991 | WIPO . |
| WO 93/20185 | 10/1993 | WIPO . |
| WO 94/17192 | 8/1994 | WIPO . |
| WO 94/21287 | 9/1994 | WIPO . |
| WO 95/21862 | 8/1995 | WIPO . |
| WO 95/23814 | 9/1995 | WIPO . |
| WO 95/34638 | 12/1995 | WIPO . |

OTHER PUBLICATIONS

Berzofsky, J.A., and Berkower, I.J., "Immunogenicity and Antigen Structure," in *Fundamental Immunology, Third Edition* (Paul, W.E., Ed.) Raven Press, Ltd., New York, NY, pp. 235–274 (1993).
Disis, M.L., et al., "Peptide–Based, but Not Whole Protein, Vaccines Elicity Immunity to HER–2/neu, an Oncogenic Self–Protein," *J. Immunol.* 156:3151–3158 (1996).
Fisk, B., et al., "Identification of an Immunodominant Peptide of HER–2/neu Protooncogene Recognized by Ovarian Tumor–Specific Cytocotic T Lymphocyte Lines," *J. Exp. Med.* 181:2109–2117 (1995).
Flamand, V., et al., "Murine Dendritic Cells in Vitro with Tumor Antigen Induce Tumor Resistance in vivo," *Eur. J. Immunol.* 24:605–610 (1994).
Lin, R.–H., et al., "Induction of Autoreactive B Cells Allows Priming of Autoreactive T Cells," *J. Exp. Med.* 173:1433–1439 (1991).
Mamula, M.J., et al., "Breaking T Cell Tolerance with Foreign and Self Co–Immunogens," *J. Immunol.* 149(3) : 789–795 (1992).
Schirmbeck, R., et al., "Immunization of Mice with the N–Terminal (1–272) Fragment of Simian Virus 40 Large T Antigen (Without Adjuvants) Specifically Primes Cytotoxic T Lymphocytes," *Eur. J. Immunol.* 23:1528–1534 (1993).
Schwartz, R.H., "Immunological Tolerance," in *Fundamental Immunology, Third Edition* (Paul, W.E., Ed.) Raven Press, Ltd., New York, NY, pp. 677–720 (1993).
Tao, M.–H., and Levy, R., "Idiotype/Granulocyte–Macrophage Colony–Stimulating Factor Fusion Protein as a Vaccine for B–Cell Lymphoma," *Nature* 362:755 (1993).
Sharief, R.S., et al., "Human Prostatic Acid Phosphatase: cDNA Cloning, Gene Mapping and Protein Sequence Homology with Lysosomal Acid Phophatase," *Biochemical and Biophysical Research Communications*, 160(1): 79–86 (1989).
Stauss H.J., et al., "Induction of Cytotoxic T Lymphocytes with Peptides in vitro: Identification of Candidate T–cell Epitopes in Human Papilloma Virus," *Proc. Natl. Acad. Sci. USA*, 89:7871–7875 (1992).
Takahashi, H., et al., "Induction of CD8$^+$ Cytotoxic T Cells by Immunization with Purified HIV–1 Envelope Protein in ISCOMs," *Nature*, 344:873–875 (1990).
Richard et al (Bone Marrow Transplantation vol. 11, Jun. 1993 pp. 473–478.
Grabbe et al (J. Of Leukocyte Biology vol. 55 pp. 695–701), Jun. 1994.
Sunshine et al (J. Of Investigative Dematology vol. 85 pp. 1105–1145), 1985.
Jones et al Eur. J. Clin. Micro. & Infect. Disease 1994 (13) 547–53.
Hodgson et al Eur. J. Biochem. 212 441–446 1993.
Lopez et al Eur. J. Immunology 1993 23: 217–223.
Boog et al J. Immunol. 140 (10) 1988 pp. 3331–3337.
Vihko et al Cancer Research 41 Mar. 1981 pp. 1180–1183.
Dranoff et al Proc. Natl. Acad. Sci. 90:3539 1993.

*Primary Examiner*—Anthony C. Caputa
*Assistant Examiner*—Mark Navarro
*Attorney, Agent, or Firm*—Linda R. Judge; Dehlinger & Associates

[57] ABSTRACT

Disclosed are therapeutic compositions and methods for inducing cytotoxic T cell responses in vitro and in vivo. The therapeutic compositions consist of antigen presenting cells activated by contact with a polypeptide complex constructed by joining together a dendritic cell-binding protein and a polypeptide antigen. Also disclosed are expression vectors and systems for producing the polypeptide complexes.

7 Claims, 7 Drawing Sheets

```
CGGCTCTCCT CAACATGAGA GCTGCACCCC TCCTCCTGGC CAGGGCAGCA         50
              MetArg AlaAlaProL euLeuLeuAl aArgAlaAla
AGCCTTAGCC TTGGCTTCTT GTTTCTGCTT TTTTTCTGGC TAGACCGAAG        100
SerLeuSerL euGlyPheLe uPheLeuLeu PhePheTrpL euAspArgSe
TGTACTAGCC AAGGAGTTGA AGTTTGTGAC TTTGGTGTTT CGGCATGGAG        150
rValLeuAla LysGluLeuL ysPheValTh rLeuValPhe ArgHisGlyA
ACCGAAGTCC CATTGACACC TTTCCCACTG ACCCCATAAA GGAATCCTCA        200
spArgSerPr oIleAspThr PheProThrA spProIleLy sGluSerSer
TGGCCACAAG GATTTGGCCA ACTCACCCAG CTGGGCATGG AGCAGCATTA        250
TrpProGlnG lyPheGlyGl nLeuThrGln LeuGlyMetG luGlnHisTy
TGAACTTGGA GAGTATATAA GAAAGAGATA TAGAAAATTC TTGAATGAGT        300
rGluLeuGly GluTyrIleA rgLysArgTy rArgLysPhe LeuAsnGluS
CCTATAAACA TGAACAGGTT TATATTCGAA GCACAGACGT TGACCGGACT        350
erTyrLysHi sGluGlnVal TyrIleArgS erThrAspVa lAspArgThr
TTGATGAGTG CTATGACAAA CCTGGCAGCC CTGTTTCCCC CAGAAGGTGT        400
LeuMetSerA laMetThrAs nLeuAlaAla LeuPheProP roGluGlyVa
CAGCATCTGG AATCCTATCC TACTCTGGCA GCCCATCCCG GTGCACACAG        450
lSerIleTrp AsnProIleL euLeuTrpGl nProIlePro ValHisThrV
TTCCTCTTTC TGAAGATCAG TTGCTATACC TGCCTTTCAG GAACTGCCCT        500
alProLeuSe rGluAspGln LeuLeuTyrL euProPheAr gAsnCysPro
CGTTTTCAAG AACTTGAGAG TGAGACTTTG AAATCAGAGG AATTCCAGAA        550
ArgPheGlnG luLeuGluSe rGluThrLeu LysSerGluG luPheGlnLy
GAGGCTGCAC CCTTATAAGG ATTTTATAGC TACCTTGGGA AAACTTTCAG        600
sArgLeuHis ProTyrLysA spPheIleAl aThrLeuGly LysLeuSerG
GATTACATGG CCAGGACCTT TTTGGAATTT GGAGTAAAGT CTACGACCCT        650
lyLeuHisGl yGlnAspLeu PheGlyIleT rpSerLysVa lTyrAspPro
TTATATTGTG AGAGTGTTCA CAATTTCACT TTACCCTCCT GGGCCACTGA        700
LeuTyrCysG luSerValHi sAsnPheThr LeuProSerT rpAlaThrGl
GGACACCATG ACTAAGTTGA GAGAATTGTC AGAATTGTCC CTCCTGTCCC        750
uAspThrMet ThrLysLeuA rgGluLeuSe rGluLeuSer LeuLeuSerL
TCTATGGAAT TCACAAGCAG AAAGAGAAAT CTAGGCTCCA AGGGGGTGTC        800
euTyrGlyIl eHisLysGln LysGluLysS erArgLeuGl nGlyGlyVal
CTGGTCAATG AAATCCTCAA TCACATGAAG AGAGCAACTC AGATACCAAG        850
LeuValAsnG luIleLeuAs nHisMetLys ArgAlaThrG lnIleProSe
CTACAAAAAA CTTATCATGT ATTCTGCGCA TGACACTACT GTGAGTGGCC        900
rTyrLysLys LeuIleMetT yrSerAlaHi sAspThrThr ValSerGlyL
TACAGATGGC GCTAGATGTT TACAACGGAC TCCTTCCTCC CTATGCTTCT        950
euGlnMetAl aLeuAspVal TyrAsnGlyL euLeuProPr oTyrAlaSer
TGCCACTTGA CGGAATTGTA CTTTGAGAAG GGGGAGTACT TTGTGGAGAT       1000
CysHisLeuT hrGluLeuTy rPheGluLys GlyGluTyrP heValGluMe
GTACTATCGG AATGAGACGC AGCACGAGCC GTATCCCCTC ATGCTACCTG       1050
tTyrTyrArg AsnGluThrG lnHisGluPr oTyrProLeu MetLeuProG
```

Fig. 1A

```
GCTGCAGCCC TAGCTGTCCT CTGGAGAGGT TTGCTGAGCT GGTTGGCCCT    1100
lyCysSerPr oSerCysPro LeuGluArgP heAlaGluLe uValGlyPro
GTGATCCCTC AAGACTGGTC CACGGAGTGT ATGACCACAA ACAGCCATCA    1150
ValIleProG lnAspTrpSe rThrGluCys MetThrThrA snSerHisGl
AGGTACTGAG GACAGTACAG ATGGATCCGC ACCCGCCCGC TCGCCCAGCC    1200
nGlyThrGlu AspSerThrA sp GlySer Al aProAlaArg SerProSerP
CCAGCACACA GCCCTGGGAG CATGTGAATG CCATCCAGGA GGCCCGGCGT    1250
roSerThrGl nProTrpGlu HisValAsnA laIleGlnGl uAlaArgArg
CTCCTGAACC TGAGTAGAGA CACTGCTGCT GAGATGAATG AAACAGTAGA    1300
LeuLeuAsnL euSerArgAs pThrAlaAla GluMetAsnG luThrValGl
AGTCATCTCA GAAATGTTTG ACCTCCAGGA GCCGACCTGC CTACAGACCC    1350
uValIleSer GluMetPheA spLeuGlnGl uProThrCys LeuGlnThrA
GCCTGGAGCT GTACAAGCAG GGCCTGCGGG GCAGCCTCAC CAAGCTCAAG    1400
rgLeuGluLe uTyrLysGln GlyLeuArgG lySerLeuTh rLysLeuLys
GGCCCCTTGA CCATGATGGC CAGCCACTAC AAACAGCACT GCCCTCCAAC    1450
GlyProLeuT hrMetMetAl aSerHisTyr LysGlnHisC ysProProTh
CCCGGAAACT TCCTGTGCAA CCCAGATTAT CACCTTTGAA AGTTTCAAAG    1500
rProGluThr SerCysAlaT hrGlnIleIl eThrPheGlu SerPheLysG
AGAACCTGAA GGACTTTCTG CTTGTCATCC CCTTTGACTG CTGGGAGCCA    1550
luAsnLeuLy sAspPheLeu LeuValIleP roPheAspCy sTrpGluPro
GTCCAGGAGT GAGACCGGCC AGATGAGGCT GGCCAAGC                 1588
ValGlnGlu. ..
```

Fig. 1B

```
mraaplllar aaslslgflf llffwldrsv laKELKFVTL VFRHGDRSPI      50

DTFPTDPIKE SSWPQGFGQL TQLGMEQHYE LGEYIRKRYR KFLNESYKHE     100

QVYIRSTDVD RTLMSAMINL AALFPPEGVS IWNPILLWQP IPVHTVPLSE     150

DQLLYLPFRN CPRFQELESE TLKSEEFQKR LHPYKDFIAT LGKLSGLHGQ    200

DLFGIWSKVY DPLYCESVHN FTLPSWATED TMIKLRELSE LSLLSLYGIH    250

KQKEKSRLQG GVLVNEILNH MKRATQIPSY KKLIMYSAHD TTVSGLQMAL    300

DVYNGLLPPY ASCHLTELYF EKGEYFVEMY YRNETQHEPY PLMLPGCSPS    350

CPLERFAELV GPVIPQDWST ECMTINSHQG TEDSTDGSAP ARSPSPSTQP    400

WEHVNAIQEA RRLLNLSRDT AAEMNETVEV ISEMFDLQEP TCLQTRLELY    450

KQGLRGSLTK LKGPLTMMAS HYKQHCPPTP ETSCATQIIT FESFKENLKD   500

FLLVIPFDCW EPVQE                                          515
```

Fig. 2

```
AGTGAGCACC ATGGAGCTGG CGGCCTTGTG CCGCTGGGGG CTCCTCCTCG CCCTCTTGCC CCCCGGAGCC GCGAG    75
           MetGluLeuA laAlaLeuCy sArgTrpGly LeuLeuLeuA laLeuLeuPr oProGlyAla AlaSe
CACCCAAGTG TGCACCGGCA CAGACATGAA GCTGCGGCTC CCTGCCAGTC CCGAGACCCA CCTGGACATG CTCCG    150
rThrGlnVal CysThrGlyT hrAspMetLy sLeuArgLeu ProAlaSerP roGluThrHi sLeuAspMet LeuAr
CCACCTCTAC CAGGGCTGCC AGGTGGTGCA GGGAAACCTG GAACTCACCT ACCTGCCCAC CAATGCCAGC CTGTC    225
gHisLeuTyr GlnGlyCysG lnValValGl nGlyAsnLeu GluLeuThrT yrLeuProTh rAsnAlaSer LeuSe
CTTCCTGCAG GATATCCAGG AGGTGCAGGG CTACGTGCTC ATCGCTCACA ACCAAGTGAG GCAGGTCCCA CTGCA    300
rPheLeuGln AspIleGlnG luValGlnGl yTyrValLeu IleAlaHisA snGlnValAr gGlnValPro LeuGl
GAGGCTGCGG ATTGTGCGAG GCACCCAGCT CTTTGAGGAC AACTATGCCC TGGCCGTGCT AGACAATGGA GACCC    375
nArgLeuArg IleValArgG lyThrGlnLe uPheGluAsp AsnTyrAlaL euAlaValLe uAspAsnGly AspPr
GCTGAACAAT ACCACCCCTG TCACAGGGGC CTCCCCAGGA GGCCTGCGGG AGCTGCAGCT TCGAAGCCTC ACAGA    450
oLeuAsnAsn ThrThrProV alThrGlyAl aSerProGly GlyLeuArgG luLeuGlnLe uArgSerLeu ThrGl
GATCTTGAAA GGAGGGTCT TGATCCAGCG GAACCCCCAG CTCTGCTACC AGGACACGAT TTTGTGGAAG GACAT    525
uIleLeuLys GlyGlyValL euIleGlnAr gAsnProGln LeuCysTyrG lnAspThrIl eLeuTrpLys AspIl
CTTCCACAAG AACAACCAGC TGGCTCTCAC ACTGATAGAC ACCAACCGCT CTCGGGCCTG CCACCCCTGT TCTCC    600
ePheHisLys AsnAsnGlnL euAlaLeuTh rLeuIleAsp ThrAsnArgS erArgAlaCy sHisProCys SerPr
GATGTGTAAG GGCTCCCGCT GCTGGGGAGA GAGTTCTGAG GATTGTCAGA GCCTGACGCG CACTGTCTGT GCCGG    675
oMetCysLys GlySerArgC ysTrpGlyGl uSerSerGlu AspCysGlnS erLeuThrAr gThrValCys AlaGl
TGGCTGTGCC CGCTGCAAGG GGCCACTGCC CACTGACTGC TGCCATGAGC AGTGTGCTGC CGGCTGCACG GGCCC    750
yGlyCysAla ArgCysLysG lyProLeuPr oThrAspCys CysHisGluG lnCysAlaAl aGlyCysThr GlyPr
CAAGCACTCT GACTGCCTGG CCTGCCTCCA CTTCAACCAC AGTGGCATCT GTGAGCTGCA CTGCCCAGCC CTGGT    825
oLysHisSer AspCysLeuA laCysLeuHi sPheAsnHis SerGlyIleC ysGluLeuHi sCysProAla LeuVa
CACCTACAAC ACAGACACGT TTGAGTCCAT GCCCAATCCC GAGGGCCGGT ACATTCGG CGCCAGCTGT GTGAC    900
lThrTyrAsn ThrAspThrP heGluSerMe tProAsnPro GluGlyArgT yrThrPheGl yAlaSerCys ValTh
TGCCTGTCCC TACAACTACC TTTCTACGGA CGTGGGATCC TGCACCCTCG TCTGCCCCCT GCACAACCAA GAGGT    975
rAlaCysPro TyrAsnTyrL euSerThrAs pValGlySer CysThrLeuV alCysProLe uHisAsnGln GluVa
GACAGCAGAG GATGGAACAC AGCGGTGTGA GAAGTGCAGC AAGCCCTGTG CCCGAGTGTG CTATGGTCTG GGCAT    1050
lThrAlaGlu AspGlyThrG lnArgCysGl uLysCysSer LysProCysA laArgValCy sTyrGlyLeu GlyMe
GGAGCACTTG CGAGAGGTGA GGGCAGTTAC ATCCAGGAGT TTGCTGGCTG CAAGAAGATC TTTGG    1125
tGluHisLeu ArgGluValA rgAlaValTh rSerAlaAsn IleGlnGluP heAlaGlyCy sLysLysIle PheGl
GAGCCTGGCA TTTCTGCCGG AGAGCTTTGA TGGGGACCCA GCCTCCAACA CTGCCCCGCT CCAGCCAGAG CAGCT    1200
ySerLeuAla PheLeuProG luSerPheAs pGlyAspPro AlaSerAsnT hrAlaProLe uGlnProGlu GlnLe
CCAAGTGTTT GAGACTCTGG AAGAGATCAC AGGTTACCTA TACATCTCAG CATGGCCGGA CAGCCTGCCT GACCT    1275
uGlnValPhe GluThrLeuG luGluIleTh rGlyTyrLeu TyrIleSerA laTrpProAs pSerLeuPro AspLe
CAGCGTCTTC CAGAACCTGC AAGTAATCCG GGGACGAATT CTGCACAATG GCGCCTACTC GCTGACCCTG CAAGG    1350
uSerValPhe GlnAsnLeuG lnValIleAr gGlyArgIle LeuHisAsnG lyAlaTyrSe rLeuThrLeu GlnGl
GCTGGGCATC AGCTGGCTGG GGCTGCGCTC ACTGAGGGAA CTGGGCAGTG GACTGGCCCT CATCCACCAT AACAC    1425
yLeuGlyIle SerTrpLeuG lyLeuArgSe rLeuArgGlu LeuGlySerG lyLeuAlaLe uIleHisHis AsnTh
CCACCTCTGC TTCGTGCACA CGGTGCCCTG GGACCAGCTC TTTCGGAACC GCACCAAGC TCTGCTCCAC ACTGC    1500
rHisLeuCys PheValHisT hrValProTr pAspGlnLeu PheArgAsnP roHisGlnAl aLeuLeuHis ThrAl
CAACCGGCCA GAGGACGAGT GTGTGGGCGA GGGCCTGGCC TGCCACCAGC TGTGCGCCCG AGGGCACTGC TGGGG    1575
aAsnArgPro GluAspGluC ysValGlyGl uGlyLeuAla CysHisGlnL euCysAlaAr gGlyHisCys TrpGl
TCCAGGGCCC ACCCAGTGTG TCAACTGCAG CCAGTTCCTT CGGGGCCAGG AGTGCGTGGA GGAATGCCGA GTACT    1650
yProGlyPro ThrGlnCysV alAsnCysSe rGlnPheLeu ArgGlyGlnG luCysValGl uGluCysArg ValLe
GCAGGGGCTC CCCAGGGAGT ATGTGAATGC CAGGCACTGT TTGCCGTGCC ACCCTGAGTG TCAGCCCCAG AATGG    1725
uGlnGlyLeu ProArgGluT yrValAsnAl aArgHisCys LeuProCysH isProGluCy sGlnProGln AsnGl
CTCAGTGACC TGTTTTGGAC CGGAGGCTGA CCAGTGTGTG GCCTGTGCCC ACTATAAGGA CCCTCCCTTC TGCGT    1800
ySerValThr CysPheGlyP roGluAlaAs pGlnCysVal AlaCysAlaH isTyrLysAs pProProPhe CysVa
GGCCCGCTGC CCCAGCGGTG TGAAACCTGA CCTCTCCTAC ATGCCCATCT GGAAGTTTCC AGATGAGGAG GGCGC    1875
lAlaArgCys ProSerGlyV alLysProAs pLeuSerTyr MetProIleT rpLysPhePr oAspGluGlu GlyAl
ATGCCAGCCT TGCCCCATCA ACTGCACCCA CTCCTGTGTG GACCTGGATG ACAAGGGCTG CCCCGCCGAG CAGAG    1950
aCysGlnPro CysProIleA snCysThrHi sSerCysVal AspLeuAsp spLysGlyCy sProAlaGlu GlnAr
AGCCAGCCCT CTGACGTCCT TCGAGGCACC CGCCCGCTCG CCCAGCCCCA GCACACAGCC CTGGGAGCAT GTGAA    2025
gAlaSerPro LeuThrSerL euGluAlaPr oAlaArgSer ProSerProS erThrGlnPr oTrpGluHis ValAs
TGCCATCCAG GAGGCCCCGC GTCTCCTGAA CCTGAGTAGA GACACTGCTG CTGAGATGAA TGAAACAGTA GAAGT    2100
nAlaIleGln GluAlaProA rgLeuLeuAs nLeuSerArg AspThrAlaA laGluMetAs nGluThrVal GluVa
CATCTCAGAA ATGTTTGACC TCCAGGAGCC GACCTGCCTA CAGACCCGCC TGGACTGTA CAAGCAGGGC CTGCG    2175
lIleSerGlu MetPheAspL euGlnGluPr oThrCysLeu GlnThrArgL euGluLeuTy rLysGlnGly LeuAr
GGGCAGCCTC ACCAAGCTCA AGGGCCCCTT GACCATGATG GCCAGCCACT ACAAACAGCA CTGCCCTCCA ACCCC    2250
gGlySerLeu ThrLysLeuL ysGlyProLe uThrMetMet AlaSerHisT yrLysGlnHi sCysProPro ThrPr
GGAAACTTCC TGTGCAACCC AGATTATCAC CTTTGAAAGT TTCAAAGAGA ACCTGAAGGA CTTTCTGCTT GTCAT    2325
oGluThrSer CysAlaThrG lnIleIleTh rPheGluSer PheLysGluA snLeuLysAs pPheLeuLeu ValI
CCCCTTTGAC TGCTGGGAGC CAGTCCAGGA GTGAGACCGG CCAGATGAGG CTGGCCAAGC    2385
eProPheAsp CysTrpGluP roValGlnGl u...
```

Fig. 8

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 1588 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO

-continued (iv) ANTI-SENSE: NO (vi) ORIGINAL SOURCE:
         (A) ORGANISM: Homo sapiens
         (C) INDIVIDUAL ISOLATE: Prostatic acid phosphatase-GM-CSF
             fusion gene; Fig. 1

(vii) IMMEDIATE SOURCE:
         (A) LIBRARY: prostate carcinoma LnCaP.FGC; PBMC (xi) SEQUENCE DESCRIPTION: SEQ ID NO:1:

```
CGGCTCTCCT CAACATGAGA GCTGCACCCC TCCTCCTGGC CAGGGCAGCA AGCCTTAGCC      60

TTGGCTTCTT GTTTCTGCTT TTTTTCTGGC TAGACCGAAG TGTACTAGCC AAGGAGTTGA     120

AGTTTGTGAC TTTGGTGTTT CGGCATGGAG ACCGAAGTCC CATTGACACC TTTCCCACTG     180

ACCCCATAAA GGAATCCTCA TGGCCACAAG GATTTGGCCA ACTCACCCAG CTGGGCATGG     240

AGCAGCATTA TGAACTTGGA GAGTATATAA GAAAGAGATA TAGAAAATTC TTGAATGAGT     300

CCTATAAACA TGAACAGGTT TATATTCGAA GCACAGACGT TGACCGGACT TTGATGAGTG     360

CTATGACAAA CCTGGCAGCC CTGTTTCCCC CAGAAGGTGT CAGCATCTGG AATCCTATCC     420

TACTCTGGCA GCCCATCCCG GTGCACACAG TTCCTCTTTC TGAAGATCAG TTGCTATACC     480

TGCCTTTCAG GAACTGCCCT CGTTTTCAAG AACTTGAGAG TGAGACTTTG AAATCAGAGG     540

AATTCCAGAA GAGGCTGCAC CCTTATAAGG ATTTTATAGC TACCTTGGGA AAACTTTCAG     600

GATTACATGG CCAGGACCTT TTTGGAATTT GGAGTAAAGT CTACGACCCT TTATATTGTG     660

AGAGTGTTCA CAATTTCACT TTACCCTCCT GGGCCACTGA GGACACCATG ACTAAGTTGA     720

GAGAATTGTC AGAATTGTCC CTCCTGTCCC TCTATGGAAT TCACAAGCAG AAAGAGAAAT     780

CTAGGCTCCA AGGGGGTGTC CTGGTCAATG AAATCCTCAA TCACATGAAG AGAGCAACTC     840

AGATACCAAG CTACAAAAAA CTTATCATGT ATTCTGCGCA TGACACTACT GTGAGTGGCC     900

TACAGATGGC GCTAGATGTT TACAACGGAC TCCTTCCTCC CTATGCTTCT TGCCACTTGA     960

CGGAATTGTA CTTTGAGAAG GGGGAGTACT TTGTGGAGAT GTACTATCGG AATGAGACGC    1020

AGCACGAGCC GTATCCCCTC ATGCTACCTG GCTGCAGCCC TAGCTGTCCT CTGGAGAGGT    1080

TTGCTGAGCT GGTTGGCCCT GTGATCCCTC AAGACTGGTC CACGGAGTGT ATGACCACAA    1140

ACAGCCATCA AGGTACTGAG GACAGTACAG ATGGATCCGC ACCCGCCCGC TCGCCCAGCC    1200

CCAGCACACA GCCCTGGGAG CATGTGAATG CCATCCAGGA GGCCCGGCGT CTCCTGAACC    1260

TGAGTAGAGA CACTGCTGCT GAGATGAATG AAACAGTAGA AGTCATCTCA GAAATGTTTG    1320

ACCTCCAGGA GCCGACCTGC CTACAGACCC GCCTGGAGCT GTACAAGCAG GGCCTGCGGG    1380

GCAGCCTCAC CAAGCTCAAG GGCCCCTTGA CCATGATGGC CAGCCACTAC AAACAGCACT    1440

GCCCTCCAAC CCCGGAAACT TCCTGTGCAA CCCAGATTAT CACCTTTGAA AGTTTCAAAG    1500

AGAACCTGAA GGACTTTCTG CTTGTCATCC CCTTTGACTG CTGGGAGCCA GTCCAGGAGT    1560

GAGACCGGCC AGATGAGGCT GGCCAAGC                                       1588
```

(2) INFORMATION FOR SEQ ID NO:2:

(i) SEQUENCE CHARACTERISTICS:
         (A) LENGTH: 515 amino acids
         (B) TYPE: amino acid
         (D) TOPOLOGY: linear (ii) MOLECULE TYPE: protein (iii) HYPOTHETICAL: NO -continued (vi) ORIGINAL SOURCE:
    (A) ORGANISM: Homo sapiens
    (C) INDIVIDUAL ISOLATE: Prostatic acid phosphatase-GM-CSF
        fusion protein; Fig. 1

(xi) SEQUENCE DESCRIPTION: SEQ ID NO:2:

```
Met Arg Ala Ala Pro Leu Leu Ala Arg Ala Ser Leu Ser Leu
1               5                   10                  15

Gly Phe Leu Phe Leu Leu Phe Phe Trp Leu Asp Arg Ser Val Leu Ala
                20                  25                  30

Lys Glu Leu Lys Phe Val Thr Leu Val Phe Arg His Gly Asp Arg Ser
            35                  40                  45

Pro Ile Asp Thr Phe Pro Thr Asp Pro Ile Lys Glu Ser Ser Trp Pro
50                          55                  60

Gln Gly Phe Gly Gln Leu Thr Gln Leu Gly Met Glu Gln His Tyr Glu
65                      70                  75                  80

Leu Gly Glu Tyr Ile Arg Lys Arg Tyr Arg Lys Phe Leu Asn Glu Ser
                    85                  90                  95

Tyr Lys His Glu Gln Val Tyr Ile Arg Ser Thr Asp Val Asp Arg Thr
                100                     105                 110

Leu Met Ser Ala Met Thr Asn Leu Ala Ala Leu Phe Pro Pro Glu Gly
                115                     120                 125

Val Ser Ile Trp Asn Pro Ile Leu Leu Trp Gln Pro Ile Pro Val His
                130                     135                 140

Thr Val Pro Leu Ser Glu Asp Gln Leu Leu Tyr Leu Pro Phe Arg Asn
145                     150                 155                 160

Cys Pro Arg Phe Gln Glu Leu Glu Ser Glu Thr Leu Lys Ser Glu Glu
                    165                 170                 175

Phe Gln Lys Arg Leu His Pro Tyr Lys Asp Phe Ile Ala Thr Leu Gly
                180                     185                 190

Lys Leu Ser Gly Leu His Gly Gln Asp Leu Phe Gly Ile Trp Ser Lys
                195                     200                 205

Val Tyr Asp Pro Leu Tyr Cys Glu Ser Val His Asn Phe Thr Leu Pro
                210                     215                 220

Ser Trp Ala Thr Glu Asp Thr Met Thr Lys Leu Arg Glu Leu Ser Glu
225                     230                 235                 240

Leu Ser Leu Leu Ser Leu Tyr Gly Ile His Lys Gln Lys Glu Lys Ser
                    245                 250                 255

Arg Leu Gln Gly Gly Val Leu Val Asn Glu Ile Leu Asn His Met Lys
                260                     265                 270

Arg Ala Thr Gln Ile Pro Ser Tyr Lys Lys Leu Ile Met Tyr Ser Ala
                275                     280                 285

His Asp Thr Thr Val Ser Gly Leu Gln Met Ala Leu Asp Val Tyr Asn
                290                     295                 300

Gly Leu Leu Pro Pro Tyr Ala Ser Cys His Leu Thr Glu Leu Tyr Phe
305                     310                 315                 320

Glu Lys Gly Glu Tyr Phe Val Glu Met Tyr Tyr Arg Asn Glu Thr Gln
                    325                 330                 335

His Glu Pro Tyr Pro Leu Met Leu Pro Gly Cys Ser Pro Ser Cys Pro
                340                     345                 350

Leu Glu Arg Phe Ala Glu Leu Val Gly Pro Val Ile Pro Gln Asp Trp
                355                     360                 365

Ser Thr Glu Cys Met Thr Thr Asn Ser His Gln Gly Thr Glu Asp Ser
370                     375                 380
```

```
Thr Asp Gly Ser Ala Pro Ala Arg Ser Pro Pro Ser Thr Gln Pro
385                 390                 395                 400

Trp Glu His Val Asn Ala Ile Gln Glu Ala Arg Arg Leu Leu Asn Leu
            405                 410                 415

Ser Arg Asp Thr Ala Ala Glu Met Asn Glu Thr Val Glu Val Ile Ser
            420                 425                 430

Glu Met Phe Asp Leu Gln Glu Pro Thr Cys Leu Gln Thr Arg Leu Glu
        435                 440                 445

Leu Tyr Lys Gln Gly Leu Arg Gly Ser Leu Thr Lys Leu Lys Gly Pro
    450                 455                 460

Leu Thr Met Met Ala Ser His Tyr Lys Gln His Cys Pro Pro Thr Pro
465                 470                 475                 480

Glu Thr Ser Cys Ala Thr Gln Ile Ile Thr Phe Glu Ser Phe Lys Glu
            485                 490                 495

Asn Leu Lys Asp Phe Leu Leu Val Ile Pro Phe Asp Cys Trp Glu Pro
            500                 505                 510

Val Gln Glu
        515

(2) INFORMATION FOR SEQ ID NO:3:

(i) SEQUENCE CHARACTERISTICS:
        (A) LENGTH: 2385 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: homo sapiens
        (C) INDIVIDUAL ISOLATE: GM-CSF-HER-2 fusion gene; Fig. 8

(xi) SEQUENCE DESCRIPTION: SEQ ID NO:3:

AGTGAGCACC ATGGAGCTGG CGGCCTTGTG CCGCTGGGGG CTCCTCCTCG CCCTCTTGCC      60

CCCCGGAGCC GCGAGCACCC AAGTGTGCAC CGGCACAGAC ATGAAGCTGC GGCTCCCTGC     120

CAGTCCCGAG ACCCACCTGG ACATGCTCCG CCACCTCTAC CAGGGCTGCC AGGTGGTGCA     180

GGGAAACCTG GAACTCACCT ACCTGCCCAC CAATGCCAGC CTGTCCTTCC TGCAGGATAT     240

CCAGGAGGTG CAGGGCTACG TGCTCATCGC TCACAACCAA GTGAGGCAGG TCCCACTGCA     300

GAGGCTGCGG ATTGTGCGAG GCACCCAGCT CTTTGAGGAC AACTATGCCC TGGCCGTGCT     360

AGACAATGGA GACCCGCTGA ACAATACCAC CCCTGTCACA GGGGCCTCCC CAGGAGGCCT     420

GCGGGAGCTG CAGCTTCGAA GCCTCACAGA GATCTTGAAA GGAGGGGTCT TGATCCAGCG     480

GAACCCCCAG CTCTGCTACC AGGACACGAT TTTGTGGAAG GACATCTTCC ACAAGAACAA     540

CCAGCTGGCT CTCACACTGA TAGACACCAA CCGCTCTCGG GCCTGCCACC CCTGTTCTCC     600

GATGTGTAAG GGCTCCCGCT GCTGGGGAGA GAGTTCTGAG GATTGTCAGA GCCTGACGCG     660

CACTGTCTGT GCCGGTGGCT GTGCCCGCTG CAAGGGGCCA CTGCCCACTG ACTGCTGCCA     720

TGAGCAGTGT GCTGCCGGCT GCACGGGCCC CAAGCACTCT GACTGCCTGG CCTGCCTCCA     780

CTTCAACCAC AGTGGCATCT GTGAGCTGCA CTGCCCAGCC CTGGTCACCT ACAACACAGA     840

CACGTTTGAG TCCATGCCCA ATCCCGAGGG CCGGTATACA TTCGGCGCCA GCTGTGTGAC     900

TGCCTGTCCC TACAACTACC TTTCTACGGA CGTGGGATCC TGCACCCTCG TCTGCCCCCT     960
```

-continued

```
GCACAACCAA GAGGTGACAG CAGAGGATGG AACACAGCGG TGTGAGAAGT GCAGCAAGCC    1020

CTGTGCCCGA GTGTGCTATG GTCTGGGCAT GGAGCACTTG CGAGAGGTGA GGGCAGTTAC    1080

CAGTGCCAAT ATCCAGGAGT TTGCTGGCTG CAAGAAGATC TTTGGGAGCC TGGCATTTCT    1140

GCCGGAGAGC TTTGATGGGG ACCCAGCCTC CAACACTGCC CCGCTCCAGC CAGAGCAGCT    1200

CCAAGTGTTT GAGACTCTGG AAGAGATCAC AGGTTACCTA TACATCTCAG CATGGCCGGA    1260

CAGCCTGCCT GACCTCAGCG TCTTCCAGAA CCTGCAAGTA ATCCGGGGAC GAATTCTGCA    1320

CAATGGCGCC TACTCGCTGA CCCTGCAAGG GCTGGGCATC AGCTGGCTGG GGCTGCGCTC    1380

ACTGAGGGAA CTGGGCAGTG GACTGGCCCT CATCCACCAT AACACCCACC TCTGCTTCGT    1440

GCACACGGTG CCCTGGGACC AGCTCTTTCG GAACCCGCAC CAAGCTCTGC TCCACACTGC    1500

CAACCGGCCA GAGGACGAGT GTGTGGGCGA GGGCCTGGCC TGCCACCAGC TGTGCGCCCG    1560

AGGGCACTGC TGGGGTCCAG GGCCCACCCA GTGTGTCAAC TGCAGCCAGT TCCTTCGGGG    1620

CCAGGAGTGC GTGGAGGAAT GCCGAGTACT GCAGGGGCTC CCCAGGGAGT ATGTGAATGC    1680

CAGGCACTGT TTGCCGTGCC ACCCTGAGTG TCAGCCCCAG AATGGCTCAG TGACCTGTTT    1740

TGGACCGGAG GCTGACCAGT GTGTGGCCTG TGCCCACTAT AAGGACCCTC CCTTCTGCGT    1800

GGCCCGCTGC CCCAGCGGTG TGAAACCTGA CCTCTCCTAC ATGCCCATCT GGAAGTTTCC    1860

AGATGAGGAG GGCGCATGCC AGCCTTGCCC CATCAACTGC ACCCACTCCT GTGTGGACCT    1920

GGATGACAAG GGCTGCCCCG CCGAGCGAGA GAGCCAGCCCT CTGACGTCCC TCGAGGCACC    1980

CGCCCGCTCG CCCAGCCCCA GCACACAGCC CTGGGAGCAT GTGAATGCCA TCCAGGAGGC    2040

CCGGCGTCTC CTGAACCTGA GTAGAGACAC TGCTGCTGAG ATGAATGAAA CAGTAGAAGT    2100

CATCTCAGAA ATGTTTGACC TCCAGGAGCC GACCTGCCTA CAGACCCGCC TGGAGCTGTA    2160

CAAGCAGGGC CTGCGGGGCA GCCTCACCAA GCTCAAGGGC CCCTTGACCA TGATGGCCAG    2220

CCACTACAAA CAGCACTGCC CTCCAACCCC GGAAACTTCC TGTGCAACCC AGATTATCAC    2280

CTTTGAAAGT TTCAAAGAGA ACCTGAAGGA CTTTCTGCTT GTCATCCCCT TTGACTGCTG    2340

GGAGCCAGTC CAGGAGTGAG ACCGGCCAGA TGAGGCTGGC CAAGC                    2385
```

(2) INFORMATION FOR SEQ ID NO:4:

(i) SEQUENCE CHARACTERISTICS:
        (A) LENGTH: 782 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: homo sapiens
        (C) INDIVIDUAL ISOLATE: GM-CSF-Her-2 fusion protein; Fig. 8

(xi) SEQUENCE DESCRIPTION: SEQ ID NO:4:

```
Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60
```

-continued

```
Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
```

```
                  485                 490                 495
Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Leu Glu Ala
                645                 650                 655

Pro Ala Arg Ser Pro Ser Pro Ser Thr Gln Pro Trp Glu His Val Asn
            660                 665                 670

Ala Ile Gln Glu Ala Arg Arg Leu Leu Asn Leu Ser Arg Asp Thr Ala
        675                 680                 685

Ala Glu Met Asn Glu Thr Val Glu Val Ile Ser Glu Met Phe Asp Leu
    690                 695                 700

Gln Glu Pro Thr Cys Leu Gln Thr Arg Leu Glu Leu Tyr Lys Gln Gly
705                 710                 715                 720

Leu Arg Gly Ser Leu Thr Lys Leu Lys Gly Pro Leu Thr Met Met Ala
                725                 730                 735

Ser His Tyr Lys Gln His Cys Pro Pro Thr Pro Glu Thr Ser Cys Ala
            740                 745                 750

Thr Gln Ile Ile Thr Phe Glu Ser Phe Lys Glu Asn Leu Lys Asp Phe
        755                 760                 765

Leu Leu Val Ile Pro Phe Asp Cys Trp Glu Pro Val Gln Glu
770                 775                 780

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: synthetic oligonucleotide primer for
            PAP (xi) SEQUENCE DESCRIPTION: SEQ ID NO:5:

CGGCTCTCCT CAACATGAGA GC                                              22
```

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: synthetic oligonucleotide primer for
            human PAP (xi) SEQUENCE DESCRIPTION: SEQ ID NO:6:

CACAGGATCC ATCTGTACTG TCCTCAGTAC C                           31

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: synthetic oligonucleotide primer for
            human GM-CSF (xi) SEQUENCE DESCRIPTION: SEQ ID NO:7:

GACTGGATCC GCACCCGCCC GCTCGCCC                               28

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (C) INDIVIDUAL ISOLATE: synthetic oligonucleotide primer for
            human GM-CSF (xi) SEQUENCE DESCRIPTION: SEQ ID NO:8:

GATCTCTAGA GCTTGGCCAG CCTCATCTGG                            30

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA -continued

```
    (iii) HYPOTHETICAL: NO (iv) ANTI-SENSE: NO (vi) ORIGINAL SOURCE:
         (C) INDIVIDUAL ISOLATE: synthetic oligonucleotide primer for
             human GM-CSF (xi) SEQUENCE DESCRIPTION: SEQ ID NO:9:

AGACGCCGAG GATGGCC                                                    17

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
         (C) INDIVIDUAL ISOLATE: synthetic oligonucleotide primer for
             human GM-CSF (xi) SEQUENCE DESCRIPTION: SEQ ID NO:10:

CCTCTCTGGA ACAGGAAAGA TG                                              22
```

IMMUNOSTIMULATORY METHOD

FIELD OF THE INVENTION

The present invention relates to compositions and methods for stimulation of specific cellular immune responses in vivo. More specifically, the invention is concerned with elimination of tumor cells by cytotoxic T-lymphocytes (CTL) activated in vivo or in vitro by exposure to antigen presenting cells exposed to an immunostimulatory polypeptide complex.

BACKGROUND OF THE INVENTION

The immune response of the mammalian immune system is generally divided into two general types: humoral immunity, mediated largely by circulating antibodies, and cellular immunity mediated by various forms of T-cells. Generally, extracellular antigens stimulate a humoral response, while intracellular antigens such as viruses, stimulate a cellular response.

The cellular immune response to virally infected cells and tumor cells is largely mediated by cytotoxic T-lymphocytes ($T_c$, or CTL), when they recognize foreign antigens attached to the host cell surface as part of the Major Histocompatibility Complex (MHC), and more particularly, a common form of MHC known as MHC Class I. In contrast, antigens derived from non-viral pathogens (bacteria, fungi) are generally expressed as part of an MHC Class II complex. A different subpopulation of effector T cells (cell mediated immune cells; CMI) release cytokines that activate the host cell to destroy such pathogens.

In experimental systems, tumor-antigen specific CTL are the most powerful immunological mechanism for the elimination of tumors. CTL can be induced either in vivo with vaccines or can be generated in vitro and then be re-infused into the tumor-bearing organism. The in vivo induction of CTL is typically accomplished by immunization with live virus or cells (Tanaka, et al., *J Immunol*, (1991), 147, 3646–52, Wang, et al., *Journal of Immunology*, (1995), 4685–4692, Torre-Amione, et al., *Proc Natl Acad Sci USA*, (1990), 87, 1486–90).

Except for a few special viral proteins such as the SV-40 large T-antigen and the Hepatitis B surface antigen, injection of isolated or soluble proteins does not result in induction of CTL (Schirmbeck, et al., *Eur J Immunol*, (1993), 23, 1528–34). CTL are induced when a protein enters the class I pathway of antigen processing. To enter this pathway the protein must be present in the cytosol of the APC. There it is degraded into peptides which are then transported into the endoplasmic reticulum, where they associate with nascent HLA class I molecules. These peptides are then displayed together with the class I molecules on the cell surface and can serve that are endogenously synthesized by an APC enter this pathway. Non-cellular-delivery vehicles for proteins, such as PH-sensitive liposomes, can over-come the requirement for endogenous synthesis in vivo (Nair, et al., *J Exp Med*, (1992), 175, 609–12, Nair, et al., *J Virol*, (1993), 67, 4062–9); however, these treatments are also quite toxic to the target cells.

Induction of primary HLA class I restricted CTL by pure soluble proteins in vitro has not been reported. The most common tool for ex vivo induction of primary CTL are small (8-11-mer) synthetic peptides (Stauss, et al., *Proc Natl Acad Sci USA*, (1992), 89, 7871–5, Carbone, et al., *J Exp Med*, (1988), 167, 1767–79). These synthetic peptides associate with class I molecules on the cell surface without the requirement for endogenous processing. When presented on the surface of an appropriate APC (such as a dendritic cell) they can then induce a primary CTL response. However, frequently these CTL do not protect against challenge with pathogens that endogenously synthesize the protein from which the peptide was derived because of their low T-cell receptor avidity (Speiser, et al., *J Immunol*, (1992), 149, 972–80) and because they induce reactivity with a single epitope of the target antigen.

GM-CSF is a cytokine that has pleiotropic function both in hematopoiesis as well as in immunology. GM-CSF has been shown to promote differentiation and survival of dendritic cells. GM-CSF can be used as an systemic adjuvant (Jones, et al., *Eur J Clin Microbiol Infect Dis*, (1994), 13, S47–53).

It is well known that immunization with soluble proteins can result in a significant antibody response. However, since class II restricted antigen presentation or direct B-cell stimulation is responsible for this effect, antibody induction has no predictive value for the induction of class I mediated induction of CTL. Most proteins that induce antibodies in vivo fail to induce CTL.

GM-CSF fusion proteins have been shown to induce in vivo antibody responses in a lymphoma mouse model (Levy, R. and Tao, M. -H. (1993) *Nature* 362: 755–758; Chen, et al., *Journal of Immunology*, (1995), 3105–3117). In this study, tumor idiotype fused to GM-CSF was found to be superior to the mixture of both molecules and to other conventional adjuvants for the induction of antibody responses. Contrary to other solid tumors antibodies are believed to be the effector mechanism for tumor protection and for tumor therapy in lymphoma.

Moreover, in vitro induction of immunity is generally much more difficult to achieve for both cellular and humoral responses. For instance, viral antigen-transfected fibroblasts induce Class I restricted CTL in vivo in mice but fail to do so in vitro (Kündig, et al., *Science*, (1995), 268, 1343–1347). Therefore, an antibody induction study with GM-CSF fusion proteins in vivo does not imply any of its in vitro utilities, and is particularly unpredictive of CTL induction in vitro or in vivo.

Other methods that have been used for in vitro induction of primary protein-derived CTL are osmotic shock of dendritic cells and the use of Ph-sensitive liposomes (Nair, et al., *J Exp Med*, (1992), 175, 609–12). However, such methods have been shown to be inherently ineffective and toxic to APC's, because they disrupt cellular membranes by physical and chemical force in order to release the protein antigen into the cytoplasm.

These limitations are overcome by the discovery encompassed by the present invention. It is the discovery of the present invention that a T-cell response, and specifically, an MHC-Class I mediated T-cell response, can be stimulated by an isolated or soluble protein, when it is presented to the immune system as part of a complex with a dendritic cell binding protein, and more particularly GM-CSF. It is the further discovery of the present invention that such a response can be stimulated in vitro. As discussed above, in vitro stimulation of such a response has not previously been demonstrated using a full-length soluble antigen. The present invention provides for induction by isolated or soluble proteins of cellular immunity in vitro by presenting a specific antigen to an antigen presenting cell (APC), such as a dendritic cell, as part of an immunogenic fusion protein.

An important aspect of the present invention is the choice of fusion partner protein, a dendritic cell binding protein, such as granulocyte-macrophage colony stimulating protein (GM-CSF). Without relying on any particular mechanistic theory, it is believed that the protein antigen is transported over the plasma membrane of the APC in a receptor mediated non-disruptive way. It is further believed that the dendritic cell binding portion of the fusion protein serves to preserve the viability and functionality of the APC.

An additional aspect of the invention relates to the choice of target antigen. Although several tumor related antigens have been shown to serve as targets for T-cell mediated immunity in vivo, in vitro induction by isolated soluble polypeptide antigens has not been demonstrated. (Fisk, et al., *J Exp Med*, (1995), 181, 2109–2117). In experiments carried out in support of the present invention, it has now been demonstrated that tumor associated proteins not been previously shown to be a target antigens for CTL can become such targets by priming CTL with GM-CSF fusion derivatives in vitro.

SUMMARY OF THE INVENTION

In one aspect, the invention is directed to a therapeutic composition for stimulating a cellular immune response. The composition is an isolated, stimulated potent antigen presenting cell, such as an activated dendritic cell, that is able to activate T-cells to produce a multivalent cellular immune response against a selected antigen. In general, the measured T-cell response is substantially higher than a T-cell response produced by such a potent antigen presenting cells stimulated by the selected antigen alone. In a preferred embodiment of the invention, the potent antigen presenting cell is stimulated by exposing the cell in vitro to a polypeptide complex. The polypeptide complex consists essentially of a dendritic cell-binding protein and a polypeptide antigen. Preferably, the polypeptide antigen is either a tissue-specific tumor antigen or an oncogene gene product. However, it is appreciated that other antigens, such as viral antigens can be used in such combination to produce immunostimulatory responses.

In another preferred embodiment, the dendritic cell-binding protein that forms part of the immunostimulatory polypeptide complex is GM-CSF. In a further preferred embodiment, the polypeptide antigen that forms part of the complex is the tumor-specific antigen prostatic acid phosphatase. In still further preferred embodiments, the polypeptide antigen may be any one of the oncogene product peptide antigens Her2, p21RAS, and p53. The polypeptide complex may also contain, between the dendritic cell-binding protein and the polypeptide antigen, a linker peptide.

In a related aspect, the invention includes a method of activating an isolated antigen presenting cell in vitro. According to the method, the activation includes contacting an isolated antigen presenting cell with a polypeptide complex. The polypeptide complex used in this method is as described above; that is, it consists essentially of a dendritic cell-binding protein covalently linked to a polypeptide antigen, in any of the embodiments described above. According to the method, the activated antigen presenting cell is effective to activate a T-cell to produce a multivalent cellular immune response that is substantially higher than that produced by antigen presenting cells contacted with the selected polypeptide antigen alone. In a preferred embodiment, the antigen presenting cell is a dendritic cell, isolated as described herein.

In yet another related aspect, the invention includes a method of inducing a cytotoxic T-cell response in a vertebrate subject. According to this aspect of the invention an isolated dendritic cell is contacted with an immunostimulatory polypeptide complex according to any of the embodiments described above for a period of time effective to activate the antigen presenting cell. The antigen presenting cell is then injected into the mammalian subject. In a preferred embodiment, the antigen presenting cell that is activated and injected is a dendritic cell.

In further related aspects, the invention also includes the polypeptide complexes formed as described above. As described above, such polypeptide complexes are preferably formed from a dendritic cell binding protein, preferably GM-CSF, and a polypeptide antigen. The polypeptide antigen is preferably a tissue-specific tumor antigen such as prostatic acid phosphatase (PAP), or an oncogene product, such as Her2, p21RAS, and p53; however, other embodiments, such as viral antigen antigens, are also within the contemplation of the invention.

In further related aspects, the invention also includes expression vectors and expression systems for producing the above-described immunostimulatory fusion proteins, as well as substantially purified nucleic acid molecules that encode such fusion proteins. In preferred embodiments, the nucleic acid molecules code for fusion proteins consisting essentially of GM-CSF and prostatic acid phosphatase or of GM-CSF and Her2.

The invention also includes a novel prostate carcinoma cell line, HLA A2.1 cells, that can be used a target cell for testing tumor cell killing, as described herein.

BRIEF DESCRIPTION OF THE FIGURES

FIG. 1 shows nucleic acid (SEQ ID NO: 1) and deduced amino acid sequence (SEQ ID NO: 2) of PAP-GM-CSF fusion protein having as a peptide linker gly-ser resulting from the Bam HI linker (underlined);

FIG. 2 shows the amino acid sequence of the fusion protein Human Prostatic Acid Phosphatase/Human GM-CSF (SEQ ID NO: 2), with the PAP signal sequence not present in the mature protein shown in small caps, potenent in the mature protein shown in small caps, potential N-glycosylation sites marked "C", and potential disulfide bridges marked "S—S";

FIG. 8 shows the nucleic acid (SEQ ID NO: 3) and amino acid (SEQ ID NO: 4) sequences of a GM-CSF-Her2 fusion protein in accordance with the present invention.

DETAILED DESCRIPTION OF THE INVENTION

I. Definitions

Figure 3A:
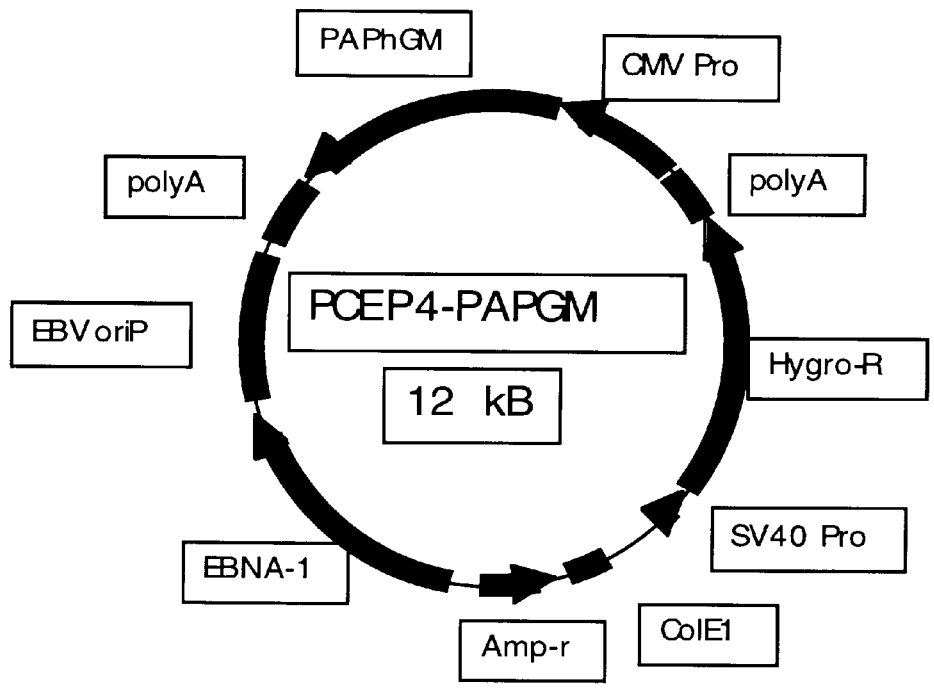
FIGS. 3A and 3B show schematic representations of PAP-GM expression vectors pCEP4 PAPGM (3A) and PAPHGM-BAC (3B) used in mammalian (293 cells) and insect (SF21) cell lines, respectively.

As used herein, the term "tissue-specific antigen" refers to an antigen that is characteristic of a tissue type, including specific tumor tissues. An example of a tissue-specific antigen expressed by a tumor tissue is the antigen prostatic acid phosphatase, which is present in over 90% of all prostate tumors. By way of contrast, B-cell lymphomas produce immunoglobulin antigens that are particular to the individual tumor. Such particular tumor antigens are not considered to fall within the definition of the term "tissue-specific antigen."

The term "oncogene product" refers to any protein coded for by a gene associated with cellular transformation. Examples of oncogene products include, for example, Her2, p21RAS, and p53.

"Antigen presenting cells" (APC) are cells that are capable of activating T cells, and include, but are not limited to, certain macrophages, B cells and dendritic cells.

"Potent antigen presenting (PAP) cells" are cells which, after being pulsed with an antigen, can activate naive CD8$^+$ cytotoxic T-lymphocytes (CTL) in a primary immune response.

The term "dendritic cell" refers to any member of a diverse population of morphologically similar cell types found in lymphoid or non-lymphoid tissues. These cells are characterized by their distinctive morphology, high levels of surface MHC-class II expression (Steinman, et al., Ann. Rev. Immunol. 9: 271 (1991); incorporated herein by reference for its description of such cells). These cells can be isolated from a number of tissue sources, and conveniently, from peripheral blood, as described herein.

The term "dendritic cell binding protein" refers to any protein for which receptors are expressed on a dendritic cell. Examples include GM-CSF, IL-1, TNF, IL-4, CD40L, CTLA4, CD28, and FLT-3 ligand.

II. Immunostimulatory Polypeptide Complexes

A. Selection of Components of the Polypeptide Complex

An immunogenic polypeptide formed in accordance with the present invention is generally characterized as an isolated polypeptide antigen which is covalently linked to a dendritic cell-binding protein.

1. Polypeptide Antigens

As stated above, isolated polypeptide antigens do not generally stimulate activation of T-cells in vivo or in vitro. It is the discovery of the present invention that certain types of polypeptide antigens, when coupled to a dendritic cell-binding proteins, such as those discussed in Section 1.b., below, stimulate T-cell activation.

The present invention identifies as particularly useful in this capacity (1) tissue-specific tumor antigens and (2) oncogene product peptide antigens.

In the context of the present invention, "tissue-specific tumor antigens" refers to antigens that are common to specific tumor types. By way of contrast, antigens that are specific to a particular individual tumor, such as the B cell lymphoma tumor-associated idiotype antigen, are distinguishable from tissue-specific tumor antigens in that they have a characteristic epitope that varies from individual to individual. Such antigens are less useful in the context of the present invention, since a immunostimulatory reagents must be tailored to the individual tumor, and consequently do not form part of the invention.

Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD 19, CD20, idiotype) have been used as targets for passive immunotherapy with monoclonal antibodies with limited success.

Thus, examples of tissue-specific tumor antigens include, but are not limited to prostatic acid phosphatase (PAP; associated with prostatic tumors), Melan-A/MART-1 (associated with melanoma; Coulie et al., 1994, *J. Exp. Med.* 180:35, Hawakami et al., 1994, *PNAS* 91:3515, Bakker et al., 1994, *J. Exp. Med.* 179:1005), tyrosinase/albino (associated with melanoma; Kawakami et al., 1994, *J. Exp. Med.*), and CD19, CD20 and CD37 (associated with lymphoma).

Likewise, oncogene product peptide antigens have been identified that are common to specific tumor types. These polypeptides will find use in the polypeptide complexes of the present invention as reagents that can be used generally to stimulate T-cell responses effective to react with tumors bearing such antigens. oncogene product peptide antigens include but are not limited to HER-2/neu (Beckmann et al., 1992, *Eur. J. Cancer* 28:322) associated with human breast and gynecological cancers, carcinoembryonic antigen (CEA) associated with cancer of the pancreas.

A variety of tumor markers are known in the art or are commercially available and include, but are not limited to the tissue-specific antigens that include cytokeratins, prostate-specific antigen (Wang et al., 1977), gp75/brown (Brichard et al., 1993, *J. Exp. Med.* 178:489) associated with melanoma, melanotransferrin (Real et al., 1984, *J. Exp. Med.* 160:1219), MUC1 (Barnd, 1989, *PNAS USA* 86:7159 and Vijayasaradhi et al., 1990, *J. Exp. Med.* 171:1375) associated with pancreas and breast cancer; oncogene/tumor suppressor genes that include EGF-R (Osborne et al., 1980), estrogen receptor, progesterone receptor, retinoblastoma gene product, myc associated with lung cancer, ras, p53, nonmutant associated with breast tumors, MAGE-1,3 (van der Bruggen et al., 1991, *Science* 254:1643 and Gaugler et al., 1994, *J. Exp. Med.* 179:921) associated with melanoma, lung, and other cancers.

Isolated viral antigens may include HIV antigens gp120, gp41, gag, RT, NEF, VIF; influenza antigens HA, core and matrix,; EBV antigens: EBNA, BFLF1, BOLF1, BGLF2, LMP2a, LMP2b, BBRF1, BBRF2, and P11L27; and human papilloma virus.

Polypeptide antigens such as those described above can be isolated, synthesized or recombinantly expressed according to methods known in the art. In most cases, DNA coding sequences have been identified for these molecules. In addition, many of the so-called "tumor markers" are available commercially. Such isolated antigens can be complexed with a dendritic cell binding protein, as discussed below, either chemically, or fusion protein constructs may be produced recombinantly, according to methods well known in the art.

As an example of the foregoing, prostatic acid phosphatase (PAP) is the prostate-specific isozyme of the ubiquitous enzyme acid phosphatase. PAP is a secreted molecule that has been identified as a serum tumor marker that is specific for prostate cancer. (Vihko, et al. , *FEBS Lett*, (1988), 236, 275–281, Solin, et al., *Biochim Biophys Acta*, (1990), 1048, 72–77). There is no evidence from the literature that PAP by itself might serve as an inducer and target of CTL. As is demonstrated below, the present invention shows that PAP can serve both as an inducer of CTL and as a target in prostate cancer cells, when combined with the dendritic cell binding protein GM-CSF and used to stimulate antigen presenting cells (exemplified by dendritic cells) that are then used to prime CTL.

2. Dendritic Cell Binding Proteins

The second component of the polypeptide complex of the present invention is a dendritic cell binding protein. As mentioned above, without relying on any particular mechanistic theory, it is believed that the presence of such a molecule in covalent complex with a protein antigen facilitates transport of the antigen over the plasma membrane of the antigen presenting cell, and more particularly, the dendritic cell, in a receptor-mediated, non-disruptive way. It is further believed that the dendritic cell binding portion of the fusion protein serves to preserve the viability and functionality of the APC.

An example of a dendritic cell binding protein is granulocyte-macrophage colony stimulating factor (GM-CSF). This glycoprotein, which has an apparent molecular weight of about 23–33,000 by SDS-PAGE, is a cytokine that has pleiotropic function both in hematopoiesis as well as in immunology. Both human and murine GM-CSF are synthesized with a 17-amino acid hydrophobic leader sequence that is proteolytically cleaved during secretion. The mature proteins are 127 (human) or 124 (murine) amino acids, and have core polypeptide molecular weights of 14,700 and 14,400, respectively, but share only 52% amino acid identity. The factor has been found to play a stimulatory role in the differentiation and survival of dendritic cells and is active in both glycosylated and de-glycosylated forms.

Human and murine GM-CSF have been shown to bind to both high affinity ($K_D$=20–60 pM) and low affinity ($K_D$=1–6 nM) binding sites on cells of the monocytemacrophage, neutrophil and eosinophil cell lineages. Competition for binding has been shown by another member of the hemopoietic colony stimulating factors, Multi-CSF, when the binding is carried out at 37°. Binding of GM-CSF to high affinity receptors results in rapid internalization and degradation of GM-CSF (Metcalf, D. and Nicola, N. A. (1995) *The Hemopoietic Colony-Stimulating Factors*, Cambridge University Press, N.Y.). These properties may be used to serve as a guide to the selection of additional dendritic cell binding proteins useful in forming immunostimulatory polypeptide complexes in accordance with the present invention.

B. Formation of Polypeptide Complexes

Polypeptide complexes can be formed by chemical means, such as by conventional coupling techniques known in the art. For example, the peptides can be coupled using a dehydrating agent such as dicyclohexylcarbodiimide (DCCI) to form a peptide bond between the two peptides. Alternatively, linkages may be formed through sulfhydryl groups, epsilon amino groups, carboxyl groups or other reactive groups present in the polypeptides, using commercially available reagents. (Pierce Co., Rockford, Ill.).

Figure 3B:
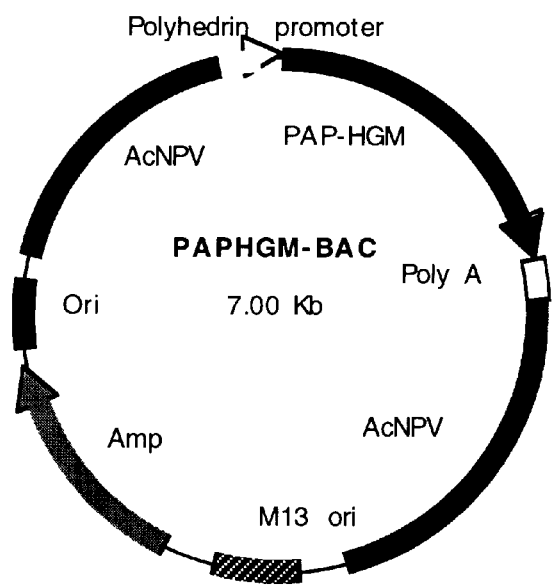

Additionally, polypeptide complexes can be formed recombinantly as fusion proteins according to methods known in the art. Example 1 details the methods used to produce a GM-CSF-PAP fusion protein in accord with the present invention. Briefly, human PAP was cloned from a prostate carcinoma cell line according to methods known in the art. The stop codon at the 3' end of the sequence was mutated away, and a Bam HI site inserted in its place, to fuse the PAP cDNA to GM-CSF DNA. GM-CSF DNA was cloned from a PBMNC library according to standard methods. A Bam HI site was inserted at the 5' end of the DNA, and an XbaI cloning site was inserted at the 3' end, along with an in-frame stop codon. PCR-generated cDNA's were digested with appropriate restriction enzymes and cloned into restriction vectors for transfection into specific mammalian or insect cell lines. FIG. 1 shows nucleic acid and deduced amino acid sequences of the PAP-GM-CSF fusion polypeptide having a gly-ser peptide linker. FIG. 2 further illustrates the fusion protein sequence with potential glycosylation sites indicated as "C" and probable disulfide bridges shown as "S—S." FIGS. 3A and 3B show schematic representations of the PAP-GM-CSF expression vectors used for transfecting mammalian (293) and insect (SF21) cell lines, respectively.

The fusion expression vectors were used to transfect COS cells (transient expression) as well as mammalian 293-EBNA cells (Invitrogen) and insect SF21 cells (Clontech, Palo Alto, Calif.). Fusion protein products were recovered from the tissue culture supernatants, and affinity purified by passage over an anti-human PAP monoclonal antibody immunoaffinity column. Analysis by SDS-PAGE revealed protein bands migrating at 75 kD and 64 kD as products from mammalian and insect cells, respectively. The 75 Kd band corresponds to a size that is approximately 19.5 Kd larger than the predicted size of the PAP-GM-CSF polypeptide backbone which is 55.5 Kd. This can be explained by the presence of 5 potential N-glycosylation sites in the sequence, glycosylation at which would increase the apparent $M_r$ of the protein, and is consistent with the fact that 293-EBNA cells contain fully functional human glycosylation machinery. The insect cell-derived fusion protein was approximately 8.5 Kd larger than the PAP-GM-CSF peptide backbone. These data are consistent with the known glycosylation patterns in Sf21 cells, which are reported to utilize N-glycosylation sites but which only add truncated carbohydrates that typically end with the addition of a single mannose residue. When PAP (prostatic acid phosphatase) GM-CSF is produced by expression in insect cells using a baculovirus vector, the recombinant protein exists as a noncovalent trimer.

Figure 4:
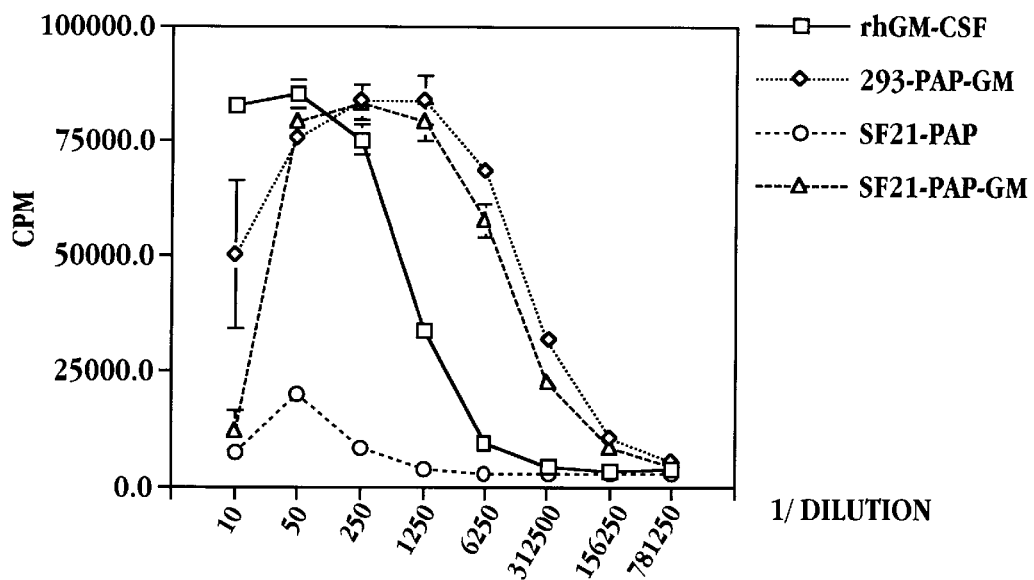
FIG. 4 shows a graph of GM-CSF bioactivity of mammalian and baculovirus-derived PAP-GM-CSF fusion proteins.
Figure 5:
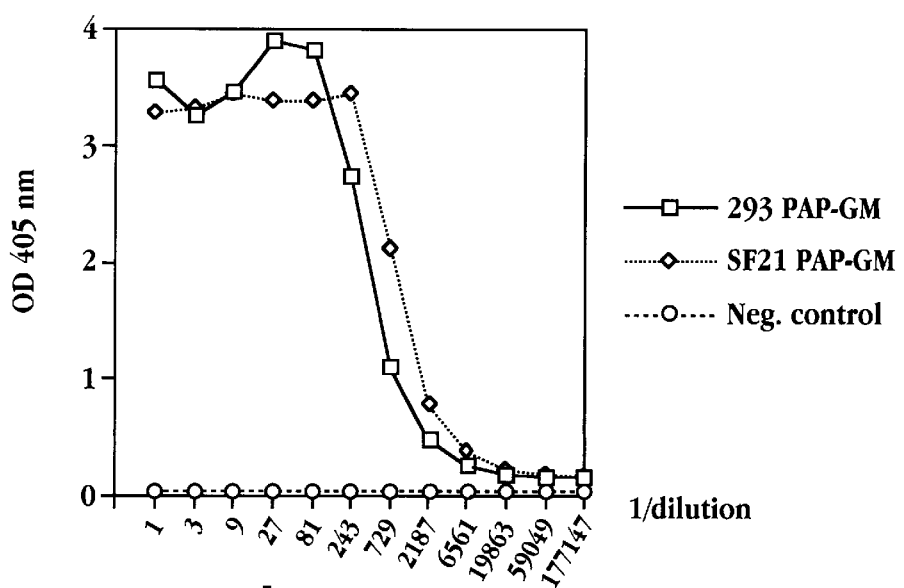
FIG. 5 shows a graph of acid phosphatase bioactivity of PAP-GM-CSF fusion proteins.

The fusion molecules were tested for PAP and GM-CSF bioactivities in appropriate assays, detailed in Example 2. Both insect and mammalian cell-derived fusion proteins exhibited GM-CSF activity, as evidenced by their ability to support growth of GM-CSF dependent cell lines (FIG. 4). Similarly, both products exhibited PAP activity (FIG. 5).

Fusion proteins constructed to incorporate oncogene product antigens are exemplified by incorporation of the oncogene product Her2. Her2 is a growth factor receptor belonging to the EGF-R family of receptors. It is overexpressed by breast cancer cells, ovarian cancer cells and a variety of other cancer cells. The cDNA coding for the extracellular domain of Her2 is cloned from a breast cancer cell line and fused to the GM-CSF CDNA, essentially as detailed for PAP-GM-CSF, above. Production of the soluble protein can be verified using Her2-specific monoclonal antibodies in an ELISA test, according to methods well-known in the art. The fusion protein includes the sequences for the extracellular domain (amino acids 1–652) of Her2 (GenBank) and GM-CSF (FIG. 8). In this particular fusion protein the two proteins are linked by a leucine/glutamic acid linker which is generated by inserting a XHO I site. Other oncogene product antigens are similarly incorporated into fusion proteins according to the methods described herein, using published sequences. In addition, other antigens, such as viral antigens, may be part of a fusion construct, according to the methods described herein.

While the foregoing description describes particular embodiments of the present invention, it will be appreciated that persons skilled in the art can substitute different antigens, vectors and expression cell lines, according to known methods, to prepare immunostimulatory polypeptide complex compositions in accordance with the principles described above. In addition, it is appreciated that the invention may also be practiced by inserting between the dendritic cell binding protein and the polypeptide antigen, a linker peptide or protein such as ubiquitin, according to recombinant methods known in the art.

III. Stimulation of T-cells

An important aspect of the present invention is the utility of the above-described polypeptide complex constructions in a method to target the antigen protein partner to Antigen Presenting Cells (APC), such as the cell type known as the "dendritic cell", described above. In accordance with the invention, the targeting occurs in a manner that results in entry into the class I pathway of antigen processing. The APC is then used to prime CTL ex vivo and in vivo, according to the methods discussed below.

Dendritic cells are highly potent APC's, and are the only APC that can prime naive CTL. While dendritic cell precursors present in human blood can take up antigen, they do not function as potent APC's. On the other hand, the mature dendritic cell is the most potent APC, but it does not take up antigen spontaneously in vitro. In the past, it was necessary to treat mature dendritic cells with physical force (liposomes, osmotic shock) or to coat them with exogenous small (8-11 amino acids in length; generally 9-mer) peptide antigens to enable them to act as APC.

The present invention enables introduction of an exogenously added protein into the class I pathway of a mature dendritic cell. Such induction can be effected in vitro, by isolating APC's such as dendritic cells, "pulsing" or contacting them with the polypeptide complex for an extended period of time, then using the pulsed APC's to stimulate autologous T-cells in vitro or in vivo. In the latter case, the pulsed APC's are administered (approximately $10^7$ cells/injection) to the subject. The response of the subject is measured by monitoring the induction of a cytolytic T-cell response, a helper T-cell response and antibody response towards the antigen in peripheral blood mononuclear cells by methods well known in the art. Multiple doses may be administered to produce an adequate response.

The use as APC's of dendritic cells stimulated by GM-CSF fusion antigens yields superior results to other approaches such as peptide pulsed dendritic cells. It is known that dendritic cells pulsed with 8-11-mer peptides induce immunity that is directed to a single T-cell epitope. Proteins incorporated into liposomes or delivered by osmotic shock induce reactivity towards multiple T-cell epitopes; however, this process is relatively ineffective due to the inherent toxicity of these treatments to dendritic cells. GM-CSF fusion antigens of the present invention, on the other hand, induce immunity towards multiple epitopes and preserve and enhance at the same time viability and function of the dendritic cell.

In practice, the compositions of the present invention are found to induce a cellular (T-cell) activation that is multivalent and substantially higher than that produced by a selected antigen alone.

In experiments carried out in support of the present invention, the fusion protein consisting of PAP and GM-CSF described in the previous section was used for in vitro introduction to dendritic cells and subsequent activation of cytolytic T cells, as detailed in Example 4. Briefly, HLA-A2.1 positive PBMNC were isolated by standard methods and primed with the fusion protein for 2–5 days. The cell mixture was depleted of $CD4^+$ T-cells, separated into high and low density fractions, and the separate cultures were restimulated weekly with autologous PAP GM-CSF pulsed APC's. Lytic potential of the T-cells present in the fractions was assessed using a standard chromium release assay using an HLA-A2.1-transgenic prostate carcinoma cell line as target. This novel cell line was constructed according to the methods detailed in Example 3 herein and is useful in screening and analysis of HLA class I restricted cytotoxic T-lymphocytes.

Figure 6:
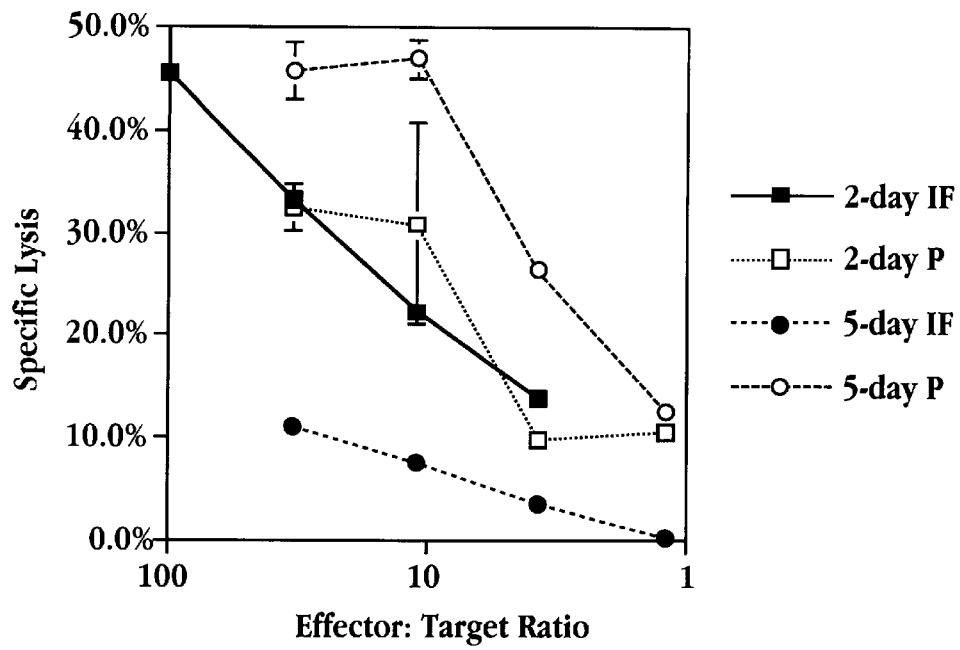
FIG. 6 shows a graph of lysis of prostate carcinoma cells by CTL primed with PAP-GM-CSF and stimulated with PAP-GM-CSF pulsed antigen presenting cells.

Results of the lysis assays are presented in FIG. 6. As shown, of the four different T-cell cultures tested, three displayed substantial dose-dependent cytotoxicity towards to prostate carcinoma target. The highest degree of cytotoxicity was seen from cells that separated into the high density pellet fraction on day 5 (open circles, 5-day P). High (open squares, 2-day P) and low (closed squares, 2-day IF) density cells primed for two days showed roughly equal potency. Cell cultures derived from day 5 low density interface fraction (closed circles, 5-day IF) displayed little or no cytotoxicity.

Figure 7:
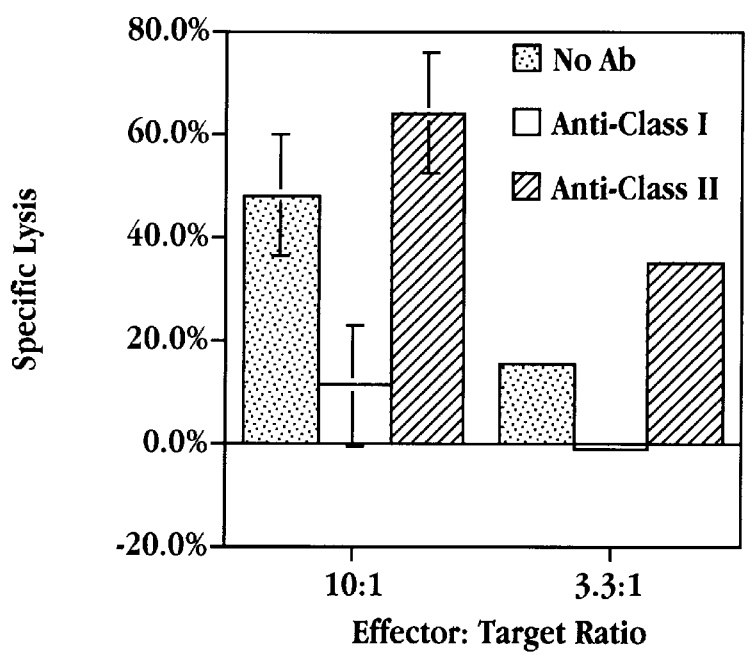
FIG. 7 shows a bar graph depicting blockade by HLA-class I blocking antibody of lysis of prostate carcinoma cells by PAP-GM-CSF primed CTL.

FIG. 7 shows that the tumor-specific cytolysis was substantially reduced in the presence of the HLA class I-specific blocking antibody W6/32 at an Effector:Target (E/T) ratio of 10:1 and is completely eliminated by the antibody at an E/T ration of 3.3/1. Control antibody CA 141 did not reduce T-cell mediated killing. These experiments demonstrate that the interaction with the target cell is mediated by via classical T-cell receptor/HLA-class I restricted antigen-specific pathway.

The foregoing results demonstrate the efficacy of fusion polypeptide complexes formed in accordance with the present invention in stimulating T-cell responses in vitro. These responses can be compared to those stimulated by the antigen alone (in the absence of the dendritic cell binding protein). In addition, their multivalent character can be tested by standard methods.

IV. Therapeutic Applications

A. In vitro/ex vivo Therapy

The present invention provides for induction by isolated or soluble proteins of cellular immunity in vitro by presenting a specific antigen to an antigen presenting cell (APC), such as a dendritic cell, as part of an immunogenic fusion protein. As discussed above such induction is not generally observed in vitro using soluble, whole antigens as induction materials.

In practice, dendritic cells are isolated from an individual, using known methods, or preferably, as described in Example 5. The dendritic cells (or other APC's) are mixed with 10 ng/ml equivalent of GM-CSF fusion antigen, as described in Example 4. The cell preparation may then be depleted of $CD4^+$ T-cells by solid phase immunoadsorption and further fractionated to enrich for cells having cytolytic activity. Doses of about $10^7$ cells are then administered to the subject by intravenous or central injection according to established procedures (e.g., infusion over 30 to 60 minutes). The responsiveness of the subject to this treatment is measured by monitoring the induction of a cytolytic T-cell response, a helper T-cell response and antibody response towards the antigen in peripheral blood mononuclear cells by methods well known in the art.

In addition to the direct in vivo administration regiment described above, the APC cells can be used, for example, in ex vivo somatic therapy, in vivo implantable devices and ex vivo extracorporeal devices. They can also be employed in the screening of antigenicity and immunogenicity of peptide epitopes from tumor- and virus-specific antigens.

In certain cases, it may be advantageous to use cells obtained from one individual to treat a condition in a second individual. For example, HIV-infected individuals with AIDS are often not able to mount anti-viral T-cell responses. In such cases, CTL can be isolated from healthy HLA-matched individuals, such as siblings, be stimulated or primed with antigen-pulsed DC in vitro, expanded, and administered back to the HIV-infected individuals.

B. In vivo Therapy

The fusion protein compositions described herein can also be administered directly to an individual as a vaccine, in order to stimulate the individual's cellular immunity pathways in vivo. Here a dose of about 5 to 200 microgram/kg fusion protein, is administered, preferably at days 0, 14 and 28 with an optional boosting dose at 6 months. The response of the subject is measured by monitoring the induction of a cytolytic T-cell response, a helper T-cell response and antibody response towards the antigen in peripheral blood mononuclear cells by methods well known in the art.

The following examples illustrate, but in no way are intended to limit the present invention.

EXAMPLE 1

Construction of PAP/GM-CSF Fusion Proteins

If not described otherwise, general cloning procedures were performed according to standard techniques as described in Sambrook, et al. *Molecular Cloning: A Laboratory Manual* (1989).

Human PAP was cloned from the prostate carcinoma cell line LnCaP.FGC (American Type Culture Collection, Rockland Md.; "ATCC"). Synthetic oligonucleotide primers containing the sequence SEQ ID NO: 5 were custom synthesized according to standard methods by Keystone Labs (Menlo Park, Calif.). These primers are homologous to the 5' end of the known PAP cDNA sequence which is published in the GenBank database.

Hind III, Mun I or Xho I restriction sites were attached, according to the requirements of the particular expression vector used. On the 3' end an oligonucleotide of the sequence SEQ ID NO: 6 was constructed that mutated away the stop codon 387 of the PAP sequence and substituted for it a Bam HI site that codes for amino acids glycine and serine. This Bam HI site was used to fuse the PAP cDNA to the GM-CSF cDNA, which was cloned from peripheral blood mononuclear cells (PBMNC), based on the sequence which is published in GenBank. At the GM-CSF 5' end a Bam HI site was attached to an oligonucleotide SEQ ID NO: 7 that is homologous to the nucleotides that code for amino acids 18–23 in the GM-CSF sequence. The 3' end of GM-CSF was generated with a an oligonucleotide SEQ ID NO: 8 that ends after the in frame stop of GM-CSF and creates an Xba I cloning site. Poly A+ RNA was isolated from cell line LnCaP.FGC and from PBMNC with the Micro Fast track kit (Invitrogen) according to the manual supplied by the manufacturer. The Poly A+ RNA was then reverse transcribed with the cDNA cycle kit (Invitrogen) according to procedures described in the accompanying manual. First strand cDNA was then subjected to 25 cycles of polymerase chain reaction (PCR) with the above described primers. The conditions on a Perkin-Elmer thermal cycler 9600 were as follows. 25 cycles of amplification were performed at: Denaturation: 94° C., 15 seconds; annealing 55° C., 15 seconds; extension 72° C., 60 seconds. The 25 cycles were followed by a final extension period of 420 seconds at 72° C. The PCR products were analyzed on agarose gels. They were digested with the appropriate restriction enzymes and cloned into the vectors pCR3 (Invitrogen) to create pCR3-PAP-GM (not shown), pCEP 4 (Invitrogen) to create pCEP4-PAP GM (FIG. 3A) and into pBacPac 8 (Clontech) to create PAPHGM-BAC (FIG. 3B). The DNA sequences of the cloned constructs were confirmed using standard methods on a fluorescent sequencer Model ABI 373A (Applied Biosystems, Foster City, Calif.). The nucleotide sequence and the deduced amino acid sequences are presented as SEQ ID NO.: 1 and SEQ ID NO: 2, in FIG. 1, respectively.

pCR3 PAP-GM was electroporated into COS-7 cells (ATCC) for transient expression experiments. After it was confirmed that a protein of the predicted size, immunological identity and function could be expressed transiently in COS-7 and 293-EBNA (Invitrogen) cells stable transfectants were generated in the human embryonic kidney cell line 293-EBNA, using an episomal expression vector pCEP4 (Invitrogen, San Diego, Calif.). After electroporation and selection in hygromycin, recombinant clones were generated by plating the cells under limiting dilution conditions and screening for PAP bioactivity in the cellular tissue culture supernatants. The highest producing clones were adapted to protein-free media and grown in CellMax hollow fiber bioreactors (Gibco, Gaithersberg, Md.). Spent media from the cultures were collected, pooled and clarified by centrifugation. They were then passaged over an immunoaffinity column that was made by coupling the human PAP-specific monoclonal antibody ATCC HB8526 (ATCC) to a Sepharose resin. After washing, the bound material was eluted at low pH, neutralized and dialyzed against physiological buffer. The eluted fraction was analyzed by denaturing SDS-PAGE electrophoresis under reducing conditions. The resulting gel showed a single protein band at 75 kD which corresponds to the predicted size of fully glycosylated PAP-GM-CSF.

PAPHGM-BAC was also used to generate a recombinant *Autographa californica* nuclear polyhedrosis virus (AcNPV, baculovirus) by homologous recombination of PAPHGM-BAC with BacPAK6 viral DNA (Clontech, Palo Alto, Calif.). Reagents were used from the BacPAK baculovirus expression system (Clontech) and procedures were carried out essentially as described in the product manual. PAPHGM-BAC and BacPAK6 were cotransfected into SF21 cells (Clontech) by lipofection. The spent tissue culture supernatant was collected on day 5. It was titered onto fresh SF21 cells which were then grown in semisolid media for another 4 days. After the monolayers were stained with neutral red, viral plaques were identified and picked with a Pasteur pipet. Recombinant plaque-purified virus was eluted into fresh media and was then used to screen for production of PAP-GM-CSF in fresh SF21 cells. Positive plaques were identified and used to generate viral stocks and recombinant protein in subsequent rounds of infecting fresh SF21 cells. The media of production cultures were collected three days after infection. They were then processed as described for PAP-GM-CSF that was derived from 293-EBNA cells. Analysis of the immunoaffinity-purified protein revealed a single protein band at 64 kD after silver staining of an SDS-PAGE gel.

EXAMPLE 2

Bioactivity of PAP-GM-CSF Fusion Proteins

PAP-GM-CSF fusion proteins from all expression systems described in Example 1 were analyzed for their ability to support the growth of GM-CSF dependent cell lines. They were also analyzed for enzymatic activity in acid phosphatase assays. Standard bioassays were used to determine the GM-CSF bioactivity.

GM-CSF Activity.

The GM-CSF dependent human erythroleukemia cell line TF-1 (ATCC, Rockville, Md.) and the acute monocytic leukemia cell line AML-193 (ATCC) were used to analyze whether GM-CSF retains its bioactivity after fusion to PAP. The cell lines which are routinely cultured in GM-CSF-containing media were starved in regular media for 24 hours before the assay. They were plated at 1500 cells per well in triplicates in tissue culture medium. Test supernatants or recombinant GM-CSF as a positive control were added to the cells. Cells were cultured for 72 hours and were then pulsed for 4 hours with 1 microcurie tritiated thymidine per well to determine rate of DNA synthesis. FIG. 4 shows that both mammalian derived and insect cell-derived PAP-GM-CSF support the growth of GM-CSF dependent cell lines. The calculated relative bioactivity of PAP-GM-CSF is 20% of the activity of control recombinant GM-CSF dependent cell lines on a molar basis.

Acid Phosphatase Activity.

The bioactivity of the second component of the fusion protein was determined in an enzymatic assay for acid phosphatase activity. Acid phosphatase was measured as the ability of the protein to hydrolyze para-nitrophenyl phosphate (PNPP) at acid pH. Briefly, the test liquid was diluted in 50 mM sodium citrate pH 4.8. pNPP is added to a final concentration of 2 mg/ml. After 30 minutes incubation at 37° C., an equal volume of 1 M NaOH was added to the reaction. Hydrolyzed pNPP under these conditions has a yellow color which can be quantified with a spectrophotometer at 405 nm. FIG. 5 shows that both mammalian derived and insect cell derived PAP-GM-CSF hydrolyzed pNPP under acid conditions.

Thus, it is clear that the original biological activity of both PAP and of GM-CSF is conserved in PAP-GM-CSF fusion proteins.

EXAMPLE 3

Generation of a Target Cell Line for HLA Class I-restricted Cytotoxic T-lymphocytes If not otherwise described, all tissue culture techniques, cell manipulations and assays were performed according to standard techniques.

In order to generate a prostate cancer cell line that could be used as a target cell on a defined genetic background an HLA A2.1-transgenic prostate cancer cell line was generated. HLA A2.1 is the best studied restriction element in human HLA class I restricted immune responses and is the most frequent allele in Caucasians. A cDNA that codes for the published sequence (GenBank) of HLA A2.1 was isolated and cloned from the lymphoblastoid cell line JY. HLA A2.1 heavy chain cDNA was amplified with the sense primer 5-SEQ ID NO: 9-3' and the anti-sense primer 5-SEQ ID NO: 10-3'. Methods and conditions were as described for PAP and GM-CSF except that the cell line JY (obtained from Dr. Ed Engleman, Stanford University Blood Bank, Stanford, Calif.) was used as starting material. The resulting gene fragment was cloned into the pCR3 vector with the TA-cloning kit (Invitrogen). The prostate carcinoma cell line LnCaP.FGC (ATCC) was transfected with this expression plasmid which confers the expression of HLA A2.1. The parent cell line does not express the A2.1 allele. After drug selection in G418 (Gibco) the resulting transfectants were selected for HLA A2.1 expression by solid phase immunoadsorption ("panning") with a HLA A2.1-specific monoclonal antibody (BB7.1, ATCC). The resulting cell line homogeneously expressed HLA-A2.1 whilst its parent remained negative. This novel transgenic cell line is uniquely useful in the screening and analysis of HLA class I restricted cytotoxic T-lymphocytes.

EXAMPLE 4

Induction of Prostate Cancer-specific CTL by PAP-GM-CSF

A T-cell in vitro priming and expansion system was used to establish the utility of PAP-GM-CSF in the generation of HLA class I restricted CTL.

HLA-A2.1-positive PBMNC were isolated by standard methods on density gradient (FICOLL-HYPAQUE, Pharmacia Fine Chemicals, Piscataway, N.J.) having a density of 1.077 gr/ml. The cells were primed with 10 ng/ml equivalent of PAP-GM-CSF for two or five days. (GM-CSF potency equivalent was measured on a GM-CSF dependent cell line as detailed in Example 3; the actual weight used was twenty-fold higher because of the different size and specific activity of PAP-GM-CSF.) The cell preparation was then depleted of CD4+ T-cells by solid phase immunoadsorption and separated into low density and high density cells over a 1.068 gr/ml density gradient. The different fractions were then cultured separately in AIM V media (Gibco, Gaithersberg, Md.) supplemented with rIL-2 (20 U/ml). Autologous PBMNC that were cultured in 20 ng/ml PAP-GM-CSF in Aim V media were used as antigen presenting cells for restimulation at weekly intervals. Lytic potential of the cells was assessed in a standard 4-hour chromium release assay with the HLA-A2-1-transgenic prostate carcinoma cell line LnCaP.FGC as a target.

FIG. 6 shows induction of Prostate-carcinoma LnCaP.FGC/A2.1-specific cytotoxic T-lymphocytes by PAP-GM-CSF pulsed antigen presenting cells. HLA-A2.1 positive PBL were primed with 10 ng/ml GM-CSF equivalents of PAP-GM-CSF for two or five days. The cultures were depleted of CD4+ T-cells and separated into low (IF) and high (P) density fractions over a Nycodenz density gradient having a density of 1.068 gr/ml.

To investigate whether the observed cytotoxicity was a HLA-class I-restricted CD8+ cytolytic T-cell mediated phenomenon a blocking assay with the monomorphic HLA class I-specific monoclonal antibody W6/32 (ATCC) antibody was performed. W6/32 blocks HLA class I mediated killing in standard assays, whilst control antibody CA141 is specific for HLA class II (DR) and will not interfere with class I restricted killing. T-cell cultures which were derived from the 5 day pellet fraction (described above) which displayed the highest cytotoxicity were used for this experiment. The T-cell lines used in experiment contained 38% CD3/CD8 positive T-cells. Their lytic potential was assessed in a standard 4-hour chromium release assay with the HLA-A2-1-transgenic Prostate carcinoma cell line LnCaP.FGC as a target. FIG. 7 shows that tumor-specific cytolysis was substantially reduced in the presence of the HLA class I blocking antibody W6/32 at an Effector:Target (E/T) ratio of 10:1 and is completely eliminated by the antibody at an E/T ration of 3.3/1. Control antibody CA 141 did not reduce T-cell mediated killing. These experiments demonstrate that the interaction with the target cell is mediated by via classical T-cell receptor/HLA-class I restricted antigen-specific pathway.

EXAMPLE 5

Preparation of Dendritic Cells

Buffy coats prepared from one unit of blood from HLA-A0201 positive volunteer healthy donors are obtained from the Stanford University Blood Center (Stanford, Calif.). Cells are harvested from the leukopacs, diluted to 60 mL using $Ca^{++}/Mg^{++}$ free phosphate buffered saline (D-PBS; Gibco Laboratories, Grand Island, N.Y.) and layered over two 15 mL columns of organosilanized colloidal silica (OCS) separation medium (prepared as described by Dorn in U.S. Pat. No. 4,927,749, incorporated herein by reference, at a density 1.0720 gr/ml, pH 7.4, 280 mOsm/kg $H_2O$) in 50 mL centrifuge tubes, preferably cell-trap tubes. The OCS medium is preferably prepared by reacting and thus blocking the silanol groups of colloidal silica (approx. 10–20 nm diameter particles) with an alkyl trimethoxy silane reagent and has the structural formula:

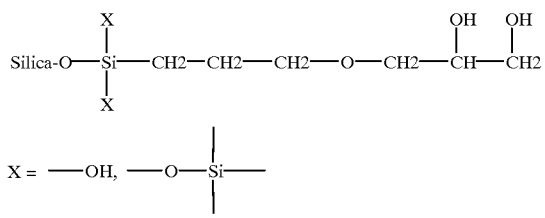

Related colloidal silicas and methods for production thereof are disclosed in U.S. Pat. No. 4,927,749 to Dorn. In a preferred embodiment, the OCS density gradient material is diluted to an appropriate specific density in a physiological salt solution supplemented with polyvinylpyrrolidone (PVP) such as PVP-10 available from Sigma Chemical Co. (St. Louis, Mo.).

The tubes are centrifuged at 1000×g for 35 minutes at room temperature. The centrifuge run is allowed to stop without braking and the peripheral blood mononuclear cells (PBMC), present at the interface, are harvested.

PBMC are resuspended in D-PBS, centrifuged once at 650×g for 10 minutes and twice more at 200×g for 5 minutes to remove platelets. Platelet-depleted PBMC are resuspended in 60 mL of D-PBS, layered on top of two columns of 15 mL of OCS (density 1.0610 gr/ml, 280 mOsm/kg $H_2O$) in a centrifuge tube and centrifuged at 650×g for 25 minutes at 4° C. without braking. The resulting interface (primarily monocytes) and pellet cells (primarily lymphocytes) are harvested and washed with D-PBS by centrifugation at room temperature (once at 650×g for 10 minutes and twice thereafter at 200×g for 5 minutes).

In instances where the dendritic cells are used to generate peptide-specific cytotoxic T lymphocytes (CTL) for purposes of elucidating their antigen presentation function, the interface fraction (mostly monocytes) is resuspended in cold pooled human AB serum (Irvine Scientific, Santa Ana, Calif.) to which an equal volume of 80% AB serum 20% dimethyl sulfoxide (DMSO) (Sigma Chemical Company, St. Louis, Mo.) is added dropwise. The resulting cell suspension is aliquoted into cryovials and frozen in liquid nitrogen. The monocytes can be used for restimulation of CTL for expansion.

The pellet fraction is resuspended in 100 mL of AB Culture Medium, inoculated into two T-75 tissue culture flasks and cultured in a humidified 5% $CO_2$ incubator for 40 hours. Following the incubation, the non adherent cells are harvested by moderate pipeting, washed and resuspended at a concentration of $2-5\times10^6$ cells/mL in AB Culture Medium. The cell suspension is overlayered over four columns of 4.0 mL OCS separation medium (density 1.0565 gr/ml, pH 7.4, 280 mOsm/kg $H_2O$), in AB Culture Medium and centrifuged at 650×g for 20 minutes at room temperature without braking.

The interface and pellet cells are harvested and washed in AB Culture Medium (Basal RPMI-1640 medium, Gibco Laboratories, Grand Island, N.Y.) by centrifugation once at 650×g for 10 minutes and twice thereafter at 200×g for 5 minutes each at room temperature. The yield and viability of both cell fractions is estimated by counting on a hemocytometer using trypan blue exclusion.

The purity of dendritic cells in the interface fraction is quantified following analysis on a flow cytometer (FACS). Dendritic cells are characterized as negative for cell phenotype markers CD3 (T lymphocytes), CD14 (monocytes), CD16 (NK cells) and CD20 (B-cells) and positive for HLA class II expression using dual staining with HLA-DR (on the FITC channel) and a cocktail of CD3, CD14, CD16, CD20 (on the PE channel). Dual staining with IgG2a on both the FITC and PE channels can be used as isotype control.

The morphology of the cells can also be evaluated using photomicroscopy. The DC enriched fraction contains large sized veiled cells with cytoplasmic processes extending from the cell surface, features characteristic of DC.

While the invention has been described with reference to specific methods and embodiments, it will be appreciated that various modifications and changes may be made without departing from the invention.

It is claimed:

1. A method of inducing a T cell-mediated cellular immune response to a soluble peptide antigen in a mammalian subject, comprising
   isolating antigen presenting cells (APCs) from the subject;
   exposing said APCs in vitro to a conjugate of granulocyte macrophage stimulating factor (GM-CSF) covalently linked to the soluble peptide antigen under conditions effective to activate the responder proliferation activity of the APCs;
   as evidenced by the ability of said APCs to stimulate proliferation of responder cells in vitro;
   administering said activated APCs to the subject.

2. The method according to claim 1, for use in treating a tumor, wherein the soluble peptide antigen is a tumor-specific antigen.

3. The method according to claim 1, wherein the conjugate further comprises, between said GM-CSF and said soluble peptide antigen, a linker peptide.

4. The method according to claim 1, wherein the antigen presenting cell is an activated dendritic cell.

5. The method according to claim 1, wherein said conjugate further comprises a fusion protein produced by translation of a continuous nucleotide coding region.

6. The method of claim 2, for use in treating prostate cancer, wherein the soluble antigen is prostatic acid phosphatase (PAP).

7. The method of claim 2, for use in treating breast cancer, wherein the soluble antigen is the Her-2 antigen.

* * * * *

(12) EX PARTE REEXAMINATION CERTIFICATE (7530th)
United States Patent
Laus et al.

(10) Number: US 6,080,409 C1
(45) Certificate Issued: May 25, 2010

(54) IMMUNOSTIMULATORY METHOD

(75) Inventors: Reiner Laus, San Carlos, CA (US);
Curtis Landon Ruegg, San Carlos, CA (US); Hongyu Wu, Palo Alto, CA (US)

(73) Assignee: TransAmerica Business Credit Corporation, Farmington, CT (US)

Reexamination Request:
No. 90/009,565, Aug. 27, 2009

Reexamination Certificate for:
Patent No.: 6,080,409
Issued: Jun. 27, 2000
Appl. No.: 08/579,823
Filed: Dec. 28, 1995

(51) Int. Cl.
*C07K 14/435* (2006.01)
*C07K 14/47* (2006.01)
*C07K 14/535* (2006.01)
*C07K 14/71* (2006.01)
*C12N 9/16* (2006.01)
*A61K 39/00* (2006.01)
*A61K 39/385* (2006.01)

(52) U.S. Cl. .............. 424/192.1; 424/193.1; 424/194.1; 424/195.11; 424/198.1; 514/2

(58) Field of Classification Search .................. None
See application file for complete search history.

(56) References Cited

U.S. PATENT DOCUMENTS

| 5,648,219 | A | 7/1997 | MacKay |
| 6,004,807 | A | 12/1999 | Banchereau |
| 6,121,044 | A | 9/2000 | Peshwa |
| 6,419,931 | B1 | 7/2002 | Vitiello |
| 2002/0098197 | A1 | 7/2002 | Sette |

FOREIGN PATENT DOCUMENTS

WO   WO09402156 A1   2/1994

OTHER PUBLICATIONS

Inaba, K., et al., "Dendritic Cells Pusled with Protein Antigens in Vitro Can Prime Antigen–Specific MHC–Restricted T–Cells in Situ," J. Exp. Med., Aug. 1990, pp. 631–640, vol. 172, The Rockfeller University Press, New York, NY, US.

*Primary Examiner*—Sharon L Turner

(57) ABSTRACT

Disclosed are therapeutic compositions and methods for inducing cytotoxic T cell responses in vitro and in vivo. The therapeutic compositions consist of antigen presenting cells activated by contact with a polypeptide complex constructed by joining together a dendritic cell-binding protein and a polypeptide antigen. Also disclosed are expression vectors and systems for producing the polypeptide complexes.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-7 is confirmed.

* * * * *